United States Patent
Zipory et al.

(10) Patent No.: US 10,973,637 B2
(45) Date of Patent: *Apr. 13, 2021

(54) IMPLANTATION OF FLEXIBLE IMPLANT

(71) Applicant: Valtech Cardio, Ltd., Or Yehuda (IL)

(72) Inventors: Yuval Zipory, Modi'in (IL); Tal Hammer, Ramat Gan (IL)

(73) Assignee: Valtech Cardio, Ltd., Or Yehuda (IL)

( * ) Notice: Subject to any disclaimer, the term of this patent is extended or adjusted under 35 U.S.C. 154(b) by 85 days.

This patent is subject to a terminal disclaimer.

(21) Appl. No.: 16/359,622

(22) Filed: Mar. 20, 2019

(65) Prior Publication Data

US 2019/0216600 A1    Jul. 18, 2019

Related U.S. Application Data

(60) Division of application No. 15/444,862, filed on Feb. 28, 2017, now Pat. No. 10,265,170, which is a
(Continued)

(51) Int. Cl.
*A61F 2/24* (2006.01)
*A61B 90/30* (2016.01)
(Continued)

(52) U.S. Cl.
CPC .......... *A61F 2/2445* (2013.01); *A61B 17/064* (2013.01); *A61B 90/30* (2016.02);
(Continued)

(58) Field of Classification Search
CPC ......... A61F 2/24; A61F 2/2448; A61F 2/2412
(Continued)

(56) References Cited

U.S. PATENT DOCUMENTS

| | | |
|---|---|---|
| 3,604,488 A | 9/1971 | Wishart et al. |
| 3,656,185 A | 4/1972 | Carpentier |

(Continued)

FOREIGN PATENT DOCUMENTS

| | | |
|---|---|---|
| EP | 1034753 A1 | 9/2000 |
| EP | 3531975 A1 | 9/2019 |

(Continued)

OTHER PUBLICATIONS

Agarwal et al, International Cardiology Perspective Functional Tricuspid Regurgitation, Circ Cardiovasc Interv 2009;2;2;565-573 (2009).

(Continued)

*Primary Examiner* — Suzette J Gherbi
(74) *Attorney, Agent, or Firm* — Thomas C. Richardson

(57) ABSTRACT

Apparatus is provided for repairing a cardiac valve, the apparatus can include a flexible annuloplasty structure having a sleeve with an elongated tubular side wall and a distal tip. A first tissue anchor can passing through the distal tip of the sleeve, and a second tissue anchor can pass through a section of the tubular side wall. The first and second tissue anchors can extend in a substantially same direction. A longitudinal portion of the tubular side wall can be disposed between the first and second tissue anchors, and have a first lateral part opposite a second lateral part and closer to the first and second tissue anchors than the second lateral part is to the first and second tissue anchors. The second lateral part can have a degree of tension that is larger than a degree of tension of the first lateral part.

20 Claims, 15 Drawing Sheets

Related U.S. Application Data continuation of application No. 14/141,228, filed on Dec. 26, 2013, now Pat. No. 9,610,162.

(51) Int. Cl.
*A61B 17/064* (2006.01)
*A61B 17/068* (2006.01)

(52) U.S. Cl.
CPC .......... *A61F 2/2466* (2013.01); *A61B 17/068* (2013.01); *A61B 2017/0649* (2013.01); *A61B 2090/306* (2016.02); *A61B 2090/309* (2016.02); *A61F 2220/0008* (2013.01); *A61F 2220/0016* (2013.01)

(58) Field of Classification Search
USPC ................................................ 623/2.36–2.38
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpenter et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Veseiy |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |

(56) References Cited

U.S. PATENT DOCUMENTS

| | | |
|---|---|---|
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,087,064 B1 | 6/2006 | Hyde |
| 7,077,850 B2 | 7/2006 | Kortenbach |
| 7,077,862 B2 | 7/2006 | Vidlund et al. |
| 7,101,395 B2 | 9/2006 | Tremulis et al. |
| 7,101,396 B2 | 9/2006 | Artof et al. |
| 7,112,207 B2 | 9/2006 | Alien et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Boiling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,780,726 B2 | 6/2010 | Seguin |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |

(56) References Cited

U.S. PATENT DOCUMENTS

| | | | |
|---|---|---|---|
| 8,187,324 B2 | 5/2012 | Webler et al. | |
| 8,202,315 B2 | 6/2012 | Hlavka et al. | |
| 8,206,439 B2 | 6/2012 | Gomez Duran | |
| 8,216,302 B2 | 7/2012 | Wilson et al. | |
| 8,231,671 B2 | 7/2012 | Kim | |
| 8,262,725 B2 | 9/2012 | Subramanian | |
| 8,265,758 B2 | 9/2012 | Policker et al. | |
| 8,277,502 B2 | 10/2012 | Miller et al. | |
| 8,287,584 B2 | 10/2012 | Salahieh et al. | |
| 8,287,591 B2 | 10/2012 | Keidar et al. | |
| 8,292,884 B2 | 10/2012 | Levine et al. | |
| 8,303,608 B2 | 11/2012 | Goldfarb et al. | |
| 8,323,334 B2 | 12/2012 | Deem et al. | |
| 8,328,868 B2 | 12/2012 | Paul et al. | |
| 8,333,777 B2 | 12/2012 | Schaller et al. | |
| 8,343,173 B2 | 1/2013 | Starksen et al. | |
| 8,343,174 B2 | 1/2013 | Goldfarb et al. | |
| 8,343,213 B2 | 1/2013 | Salahieh et al. | |
| 8,349,002 B2 | 1/2013 | Milo | |
| 8,353,956 B2 | 1/2013 | Miller et al. | |
| 8,357,195 B2 | 1/2013 | Kuehn | |
| 8,382,829 B1 | 2/2013 | Call et al. | |
| 8,388,680 B2 | 3/2013 | Starksen et al. | |
| 8,393,517 B2 | 3/2013 | Milo | |
| 8,419,825 B2 | 4/2013 | Burgler et al. | |
| 8,430,926 B2 | 4/2013 | Kirson | |
| 8,449,573 B2 | 5/2013 | Chu | |
| 8,449,599 B2 | 6/2013 | Chau et al. | |
| 8,454,686 B2 | 6/2013 | Alkhatib | |
| 8,460,370 B2 | 6/2013 | Zakay | |
| 8,460,371 B2 | 6/2013 | Hlavka et al. | |
| 8,475,491 B2 | 7/2013 | Milo | |
| 8,475,525 B2 | 7/2013 | Maisano et al. | |
| 8,480,732 B2 | 7/2013 | Subramanian | |
| 8,518,107 B2 * | 8/2013 | Tsukashima | A61F 2/2448 623/2.36 |
| 8,523,940 B2 * | 9/2013 | Richardson | A61F 2/2445 623/2.37 |
| 8,545,553 B2 * | 10/2013 | Zipory | A61F 2/2451 623/2.37 |
| 8,551,161 B2 | 10/2013 | Dolan | |
| 8,585,755 B2 | 11/2013 | Chau et al. | |
| 8,591,576 B2 | 11/2013 | Hasenkam et al. | |
| 8,608,797 B2 | 12/2013 | Gross et al. | |
| 8,628,569 B2 | 1/2014 | Benichou et al. | |
| 8,628,571 B1 * | 1/2014 | Hacohen | A61F 2/2403 623/2.2 |
| 8,641,727 B2 | 2/2014 | Starksen et al. | |
| 8,652,202 B2 | 2/2014 | Alon et al. | |
| 8,652,203 B2 | 2/2014 | Quadri et al. | |
| 8,679,174 B2 | 3/2014 | Ottma et al. | |
| 8,685,086 B2 | 4/2014 | Navia et al. | |
| 8,715,342 B2 * | 5/2014 | Zipory | A61F 2/2466 623/2.11 |
| 8,728,097 B1 | 5/2014 | Sugimoto et al. | |
| 8,728,155 B2 | 5/2014 | Montorfano et al. | |
| 8,734,467 B2 | 5/2014 | Miller et al. | |
| 8,734,699 B2 | 5/2014 | Heideman et al. | |
| 8,740,920 B2 | 6/2014 | Goldfarb et al. | |
| 8,747,463 B2 | 6/2014 | Fogarty et al. | |
| 8,778,021 B2 | 7/2014 | Cartledge | |
| 8,784,481 B2 | 7/2014 | Alkhatib et al. | |
| 8,790,367 B2 | 7/2014 | Nguyen et al. | |
| 8,790,394 B2 | 7/2014 | Miller et al. | |
| 8,795,298 B2 | 8/2014 | Hernlund et al. | |
| 8,795,355 B2 | 8/2014 | Aikhatib | |
| 8,795,356 B2 | 8/2014 | Quadri et al. | |
| 8,795,357 B2 | 8/2014 | Yohanan et al. | |
| 8,808,366 B2 | 8/2014 | Braido et al. | |
| 8,808,368 B2 | 8/2014 | Maisano et al. | |
| 8,845,717 B2 | 9/2014 | Khairkhahan et al. | |
| 8,845,723 B2 | 9/2014 | Spence et al. | |
| 8,852,261 B2 | 10/2014 | White | |
| 8,852,272 B2 * | 10/2014 | Gross | A61F 2/2418 623/2.18 |
| 8,858,623 B2 | 10/2014 | Miller et al. | |
| 8,864,822 B2 | 10/2014 | Spence et al. | |
| 8,870,948 B1 | 10/2014 | Erzberger et al. | |
| 8,870,949 B2 | 10/2014 | Rowe | |
| 8,689,861 B2 | 11/2014 | Skead et al. | |
| 8,888,843 B2 | 11/2014 | Khairkhahan et al. | |
| 8,894,702 B2 | 11/2014 | Quadri et al. | |
| 8,911,461 B2 | 12/2014 | Traynor et al. | |
| 8,911,494 B2 * | 12/2014 | Hammer | A61B 17/064 623/2.11 |
| 8,926,696 B2 | 1/2015 | Cabiri et al. | |
| 8,926,697 B2 | 1/2015 | Gross et al. | |
| 8,932,343 B2 | 1/2015 | Aikhatib et al. | |
| 8,932,348 B2 | 1/2015 | Solem et al. | |
| 8,940,044 B2 | 1/2015 | Hammer et al. | |
| 8,945,211 B2 | 2/2015 | Sugimoto | |
| 8,951,285 B2 | 2/2015 | Sugimoto et al. | |
| 8,951,286 B2 | 2/2015 | Sugimoto et al. | |
| 8,961,595 B2 | 2/2015 | Aikhatib | |
| 8,961,602 B2 | 2/2015 | Kovach et al. | |
| 8,979,922 B2 | 3/2015 | Jayasinghe et al. | |
| 8,992,604 B2 | 3/2015 | Gross et al. | |
| 9,005,273 B2 | 4/2015 | Salahieh et al. | |
| 9,011,520 B2 | 4/2015 | Miller et al. | |
| 9,011,530 B2 | 4/2015 | Reich et al. | |
| 9,017,399 B2 * | 4/2015 | Gross | A61B 17/068 623/2.11 |
| 9,023,100 B2 | 5/2015 | Quadri et al. | |
| 9,072,603 B2 | 7/2015 | Tuval et al. | |
| 9,107,749 B2 | 8/2015 | Bobo et al. | |
| 9,119,719 B2 * | 9/2015 | Zipory | A61B 17/068 |
| 9,125,632 B2 | 9/2015 | Loulmet et al. | |
| 9,125,742 B2 | 9/2015 | Yoganathan et al. | |
| 9,138,316 B2 | 9/2015 | Bielefeld | |
| 9,173,646 B2 | 11/2015 | Fabro | |
| 9,180,005 B1 | 11/2015 | Lashinski et al. | |
| 9,180,007 B2 | 11/2015 | Reich et al. | |
| 9,192,472 B2 | 11/2015 | Gross et al. | |
| 9,198,756 B2 | 12/2015 | Aklog et al. | |
| 9,226,825 B2 | 1/2016 | Starksen et al. | |
| 9,265,608 B2 | 2/2016 | Miller et al. | |
| 9,326,857 B2 | 5/2016 | Cartledge et al. | |
| 9,414,921 B2 | 8/2016 | Miller et al. | |
| 9,427,316 B2 | 8/2016 | Schweich, Jr. et al. | |
| 9,474,606 B2 | 10/2016 | Zipory et al. | |
| 9,526,613 B2 | 12/2016 | Gross et al. | |
| 9,561,104 B2 | 2/2017 | Miller et al. | |
| 9,579,090 B1 | 2/2017 | Simms et al. | |
| 9,610,162 B2 * | 4/2017 | Zipory | A61F 2/2466 |
| 9,693,865 B2 | 7/2017 | Gilmore et al. | |
| 9,730,793 B2 | 8/2017 | Reich et al. | |
| 9,601,720 B2 | 10/2017 | Gilmore et al. | |
| 9,788,941 B2 | 10/2017 | Hacohen | |
| 9,907,547 B2 | 3/2018 | Gilmore et al. | |
| 10,265,170 B2 * | 4/2019 | Zipory | A61F 2/2466 |
| 10,368,852 B2 | 8/2019 | Gerhardt et al. | |
| 2001/0021874 A1 | 9/2001 | Carpentier et al. | |
| 2002/0022862 A1 | 2/2002 | Grafton et al. | |
| 2002/0082525 A1 | 6/2002 | Oslund et al. | |
| 2002/0087048 A1 | 7/2002 | Brock et al. | |
| 2002/0103532 A1 | 8/2002 | Langberg et al. | |
| 2002/0120292 A1 | 8/2002 | Morgan | |
| 2002/0151916 A1 | 10/2002 | Muramatsu et al. | |
| 2002/0151970 A1 | 10/2002 | Garrison et al. | |
| 2002/0169358 A1 | 11/2002 | Mortier et al. | |
| 2002/0177904 A1 | 11/2002 | Huxel et al. | |
| 2002/0188301 A1 | 12/2002 | Dallara et al. | |
| 2002/0188350 A1 | 12/2002 | Arru et al. | |
| 2002/0198586 A1 | 12/2002 | Inoue | |
| 2003/0050693 A1 | 3/2003 | Quijano et al. | |
| 2003/0078465 A1 | 4/2003 | Pai et al. | |
| 2003/0078653 A1 | 4/2003 | Vesely et al. | |
| 2003/0105519 A1 | 6/2003 | Fasol et al. | |
| 2003/0114901 A1 | 6/2003 | Loeb et al. | |
| 2003/0120340 A1 | 6/2003 | Liska et al. | |
| 2003/0144657 A1 | 7/2003 | Bowe et al. | |
| 2003/0171760 A1 | 9/2003 | Gambale | |

(56) References Cited

U.S. PATENT DOCUMENTS

| | | |
|---|---|---|
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107671 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Saiahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Larnpropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzrier et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindricris et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0233239 A1* | 10/2007 | Navia .................. A61F 2/2466 623/2.37 |
| 2007/0239208 A1 | 10/2007 | Crawford |
| 2007/0244555 A1* | 10/2007 | Rafiee .................. A61F 2/2445 623/2.11 |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |

(56) References Cited

U.S. PATENT DOCUMENTS

| | | |
|---|---|---|
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0195200 A1 | 6/2008 | Vidlund et al. |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0208265 A1 | 8/2008 | Frazier et al. |
| 2008/0221672 A1 | 9/2008 | Larnphere et al. |
| 2008/0234729 A1 | 9/2008 | Page et al. |
| 2008/0262480 A1 | 10/2008 | Stahler et al. |
| 2008/0262609 A1* | 10/2008 | Gross .................. A61F 2/2466 623/2.36 |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1* | 4/2009 | Olsen ............... A61B 17/00234 623/2.37 |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152645 A1 | 6/2010 | Bloom et al. |
| 2010/0161043 A1 | 6/2010 | Maisano et al. |
| 2010/0161047 A1* | 6/2010 | Cabiri ................. A61B 17/072 623/2.37 |
| 2010/0217382 A1 | 6/2010 | Chau et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1* | 1/2011 | Lee ...................... A61F 2/2442 623/2.11 |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0123531 A1* | 5/2012 | Tsukashima .......... A61F 2/2466 623/2.37 |
| 2012/0136436 A1* | 5/2012 | Cabiri ................... A61F 2/2445 623/2.37 |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1* | 11/2012 | Hill ...................... A61F 2/2445 623/2.11 |
| 2012/0296419 A1* | 11/2012 | Richardson ........... A61F 2/2445 623/2.36 |
| 2012/0310330 A1 | 12/2012 | Buchbinder et al. |

(56) References Cited

U.S. PATENT DOCUMENTS

| | | |
|---|---|---|
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079673 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0282059 A1 | 10/2013 | Ketai et al. |
| 2013/0289718 A1 | 10/2013 | Tsukashirna et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243659 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1* | 11/2014 | Zipory ............ A61F 2/2445 623/2.11 |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1* | 10/2015 | Sheps ............ A61M 25/0133 623/2.11 |
| 2015/0282931 A1 | 10/2015 | Brunnett et al. |
| 2015/0351906 A1* | 12/2015 | Hammer ............ A61F 2/2418 623/2.11 |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0168803 A1 | 6/2018 | Pesce et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0343633 A1 | 11/2019 | Garvin et al. |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |

OTHER PUBLICATIONS

Ahmadi, A., G. Spillner, and Th Johannesson. "Hemodynamic changes following experimental production and correction of acute mitral regurgitation with an adjustable ring prosthesis," The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103, (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

(56) References Cited

OTHER PUBLICATIONS

AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology 52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence, investigative urology, 15(5), pp. 389-391.
Swenson, Orvar. "Internal device for control of urinary incontinence," Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

\* cited by examiner

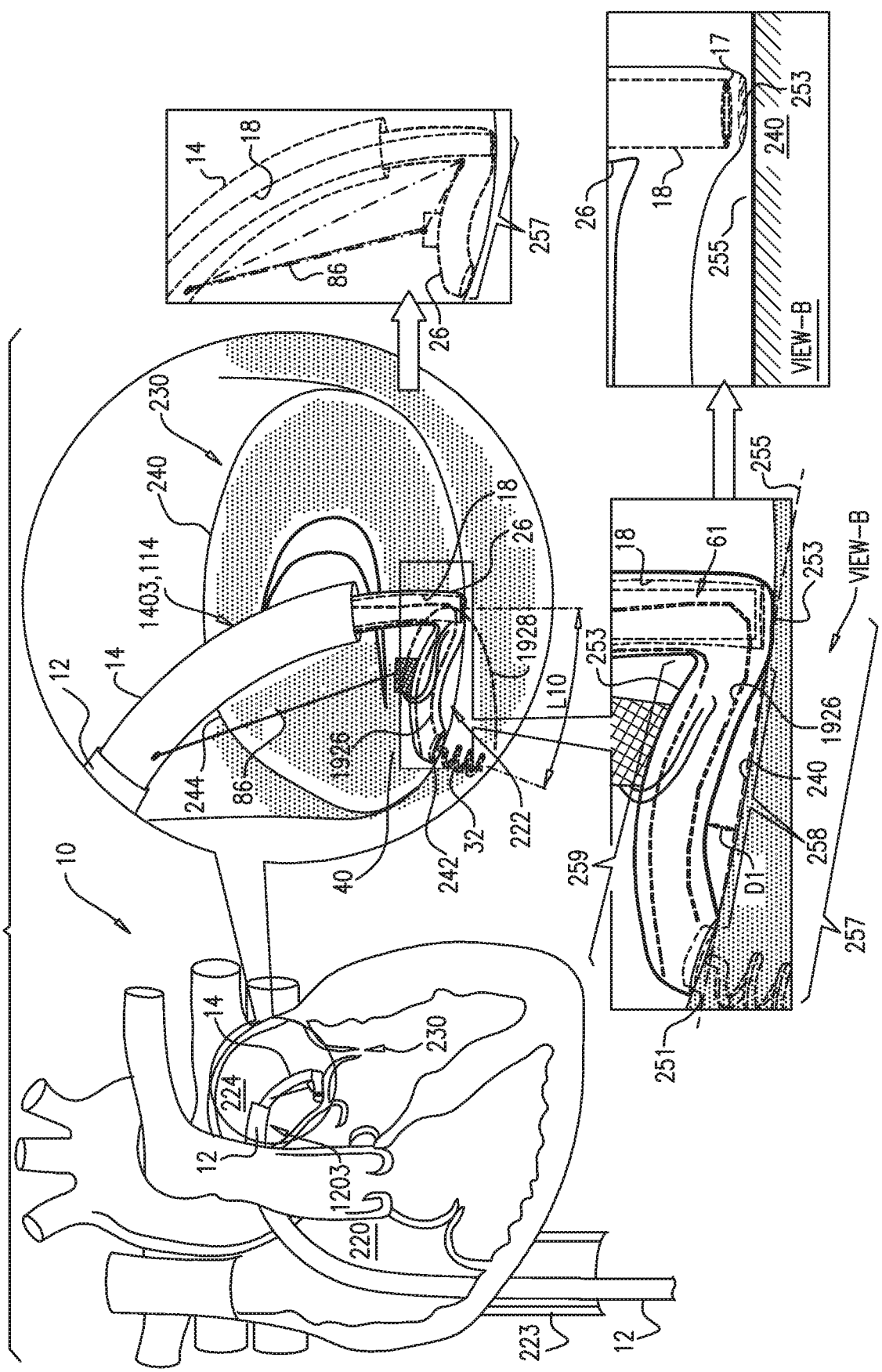

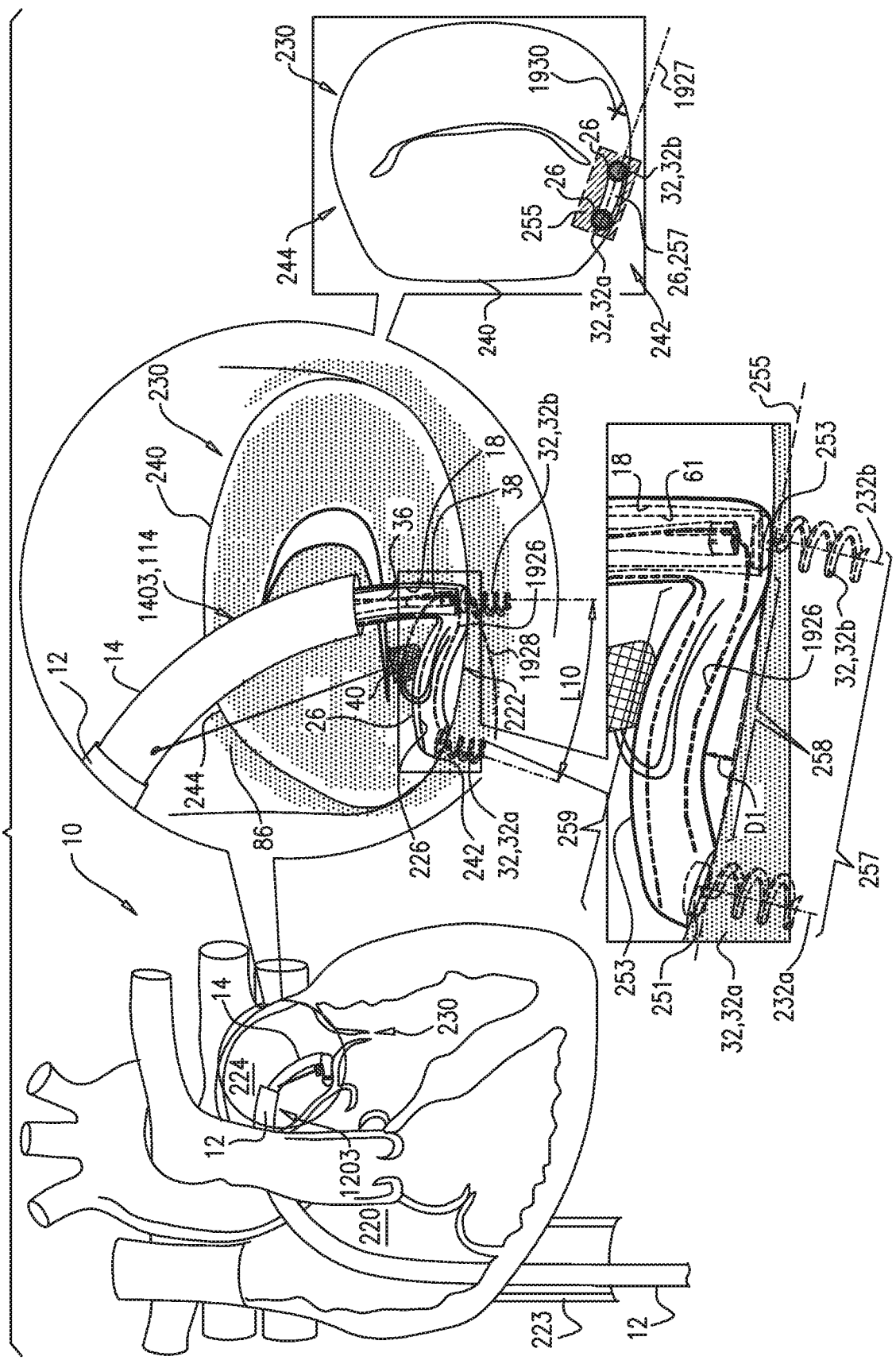

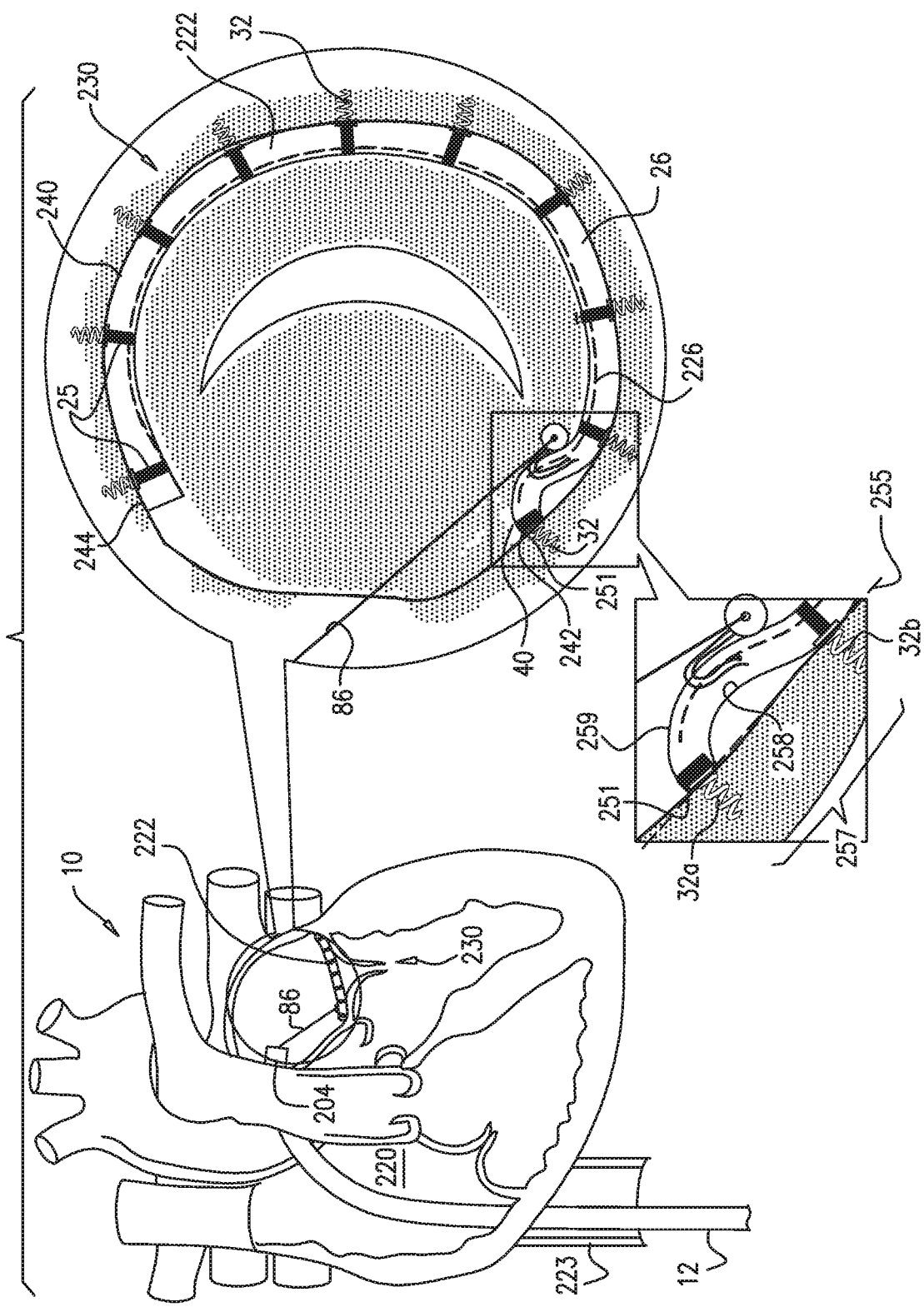

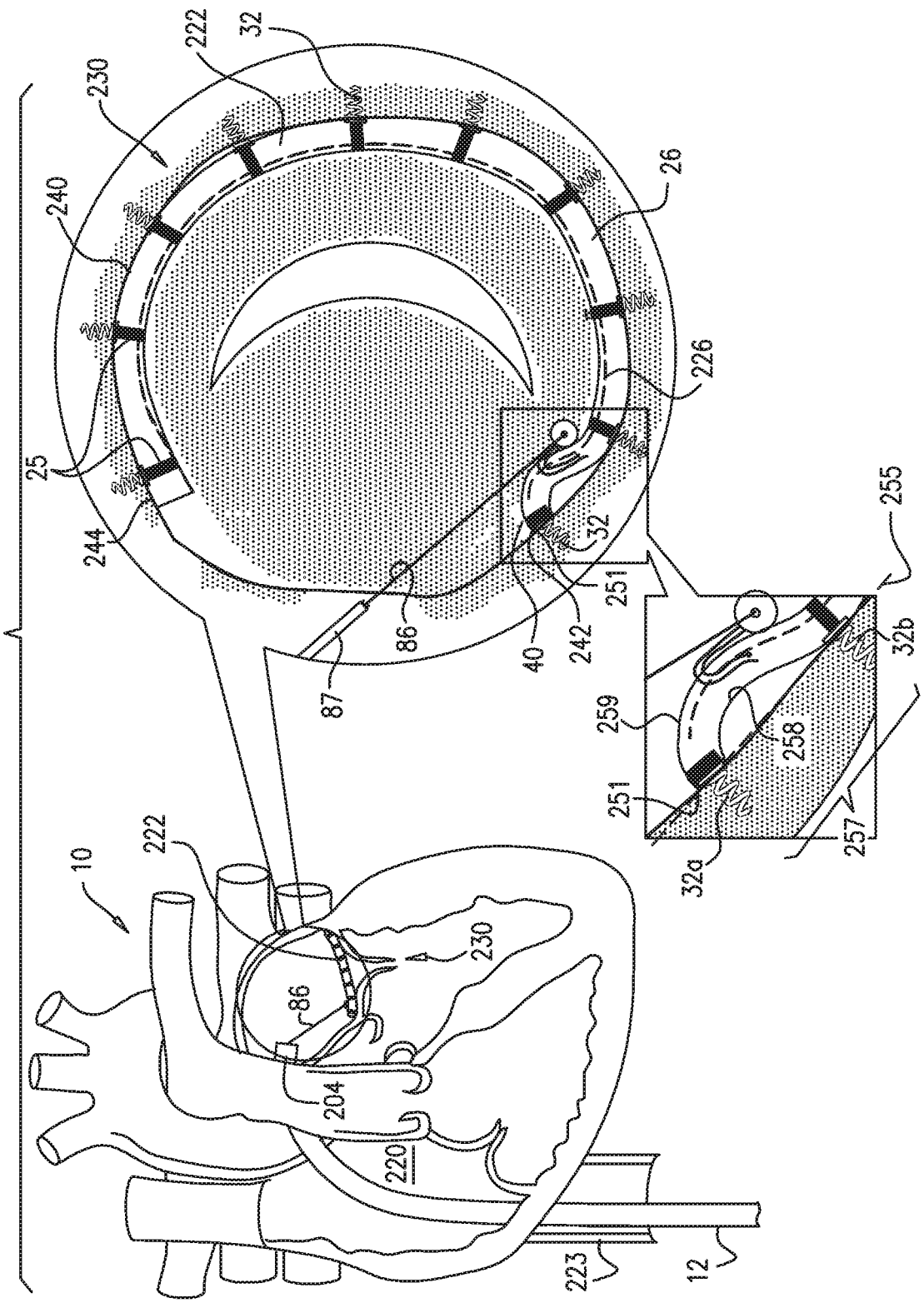

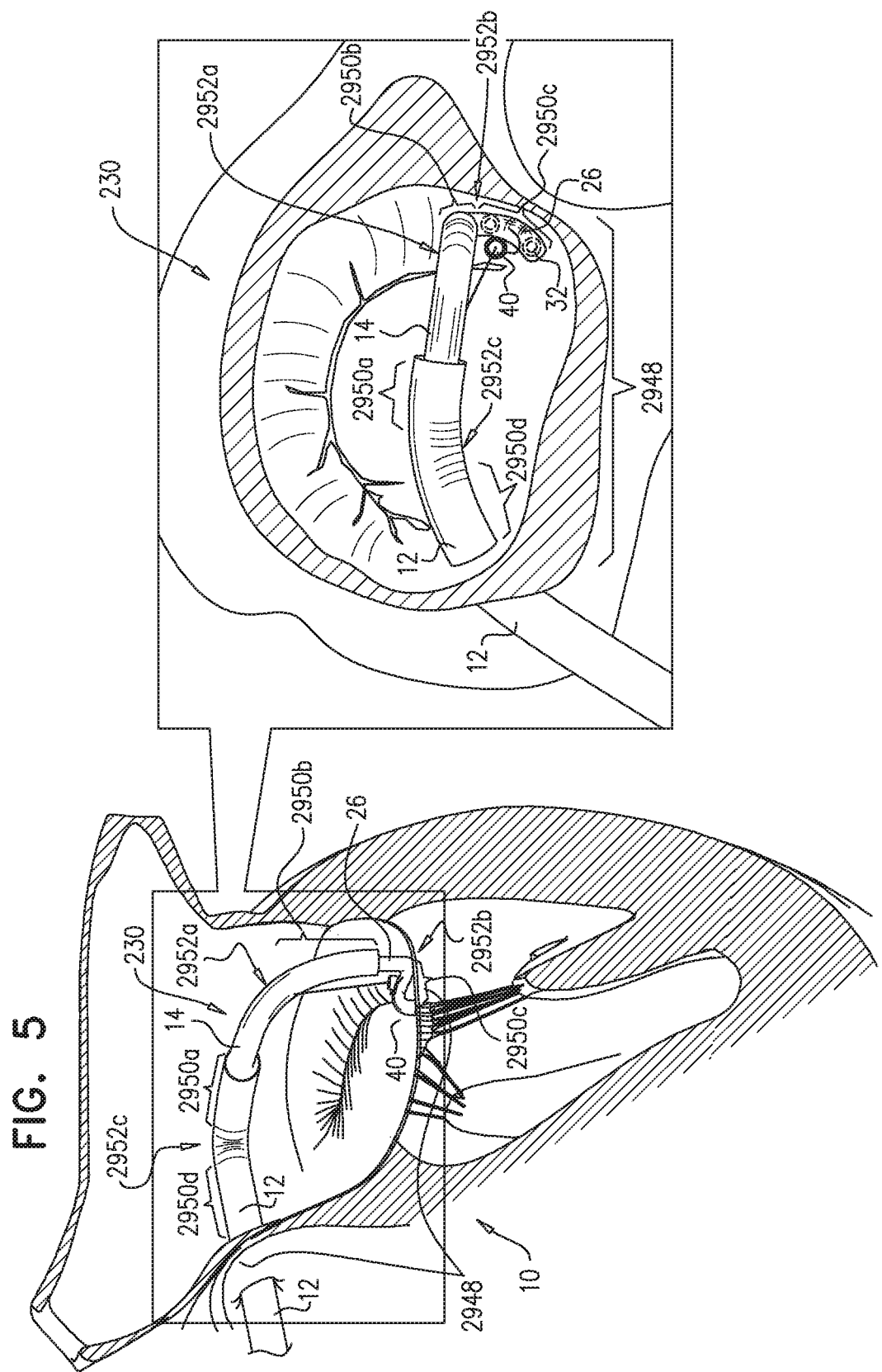

FIG. 6C
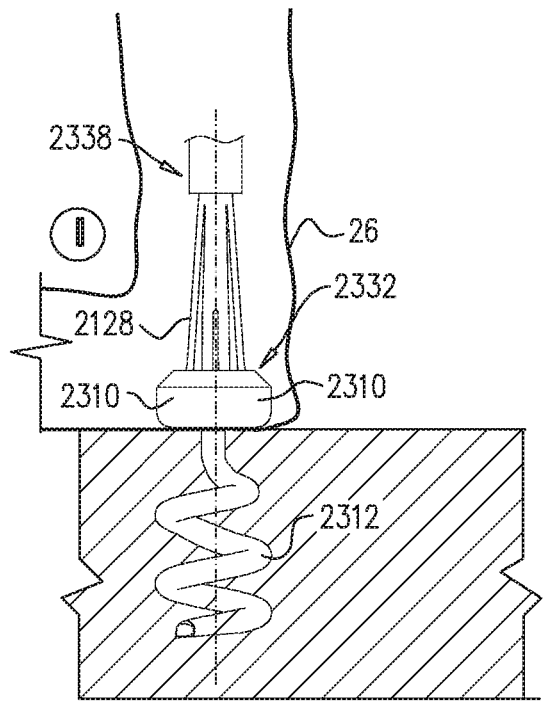
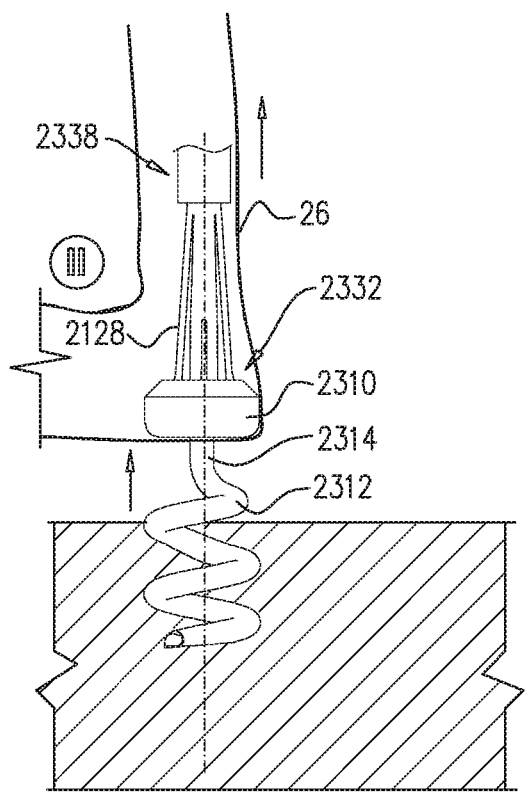
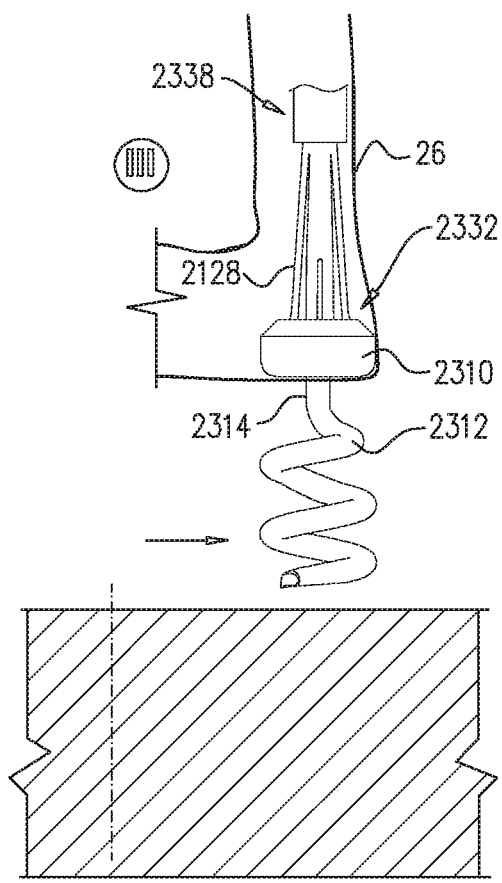
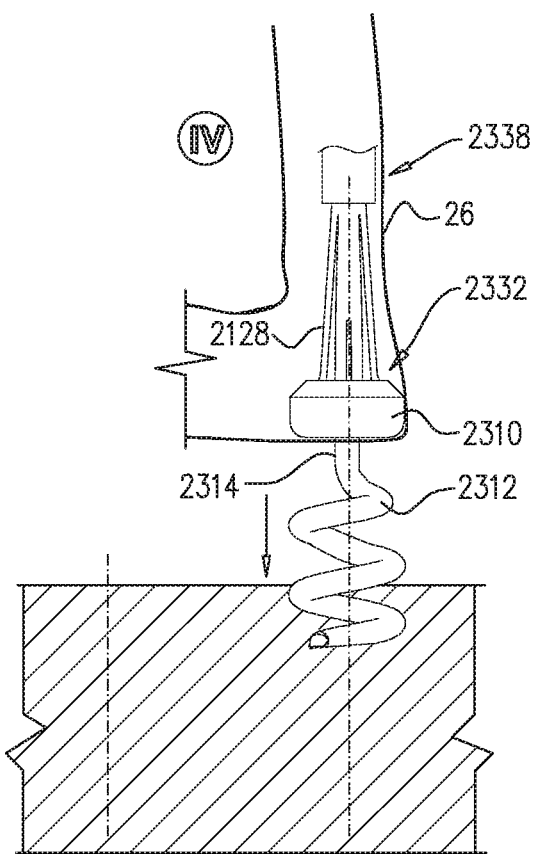

IMPLANTATION OF FLEXIBLE IMPLANT

CROSS REFERENCE TO RELATED APPLICATIONS

The present application is a divisional application of U.S. Ser. No. 15/444,862 to Zipory et al., entitled, "Implantation of flexible implant," filed on Feb. 28, 2017, which published as US 2017/0196691 and which is a continuation application of U.S. Ser. No. 14/141,228 to Zipory et al., entitled, "Implantation of flexible implant," filed on Dec. 26, 2013, which issued as U.S. Pat. No. 9,610,162. The above applications and patents are incorporated herein by reference.

FIELD OF THE INVENTION

The present invention relates in general to valve repair, and more specifically to repair of an atrioventricular valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

SUMMARY OF THE INVENTION

In some embodiments of the present invention, an adjustable annuloplasty structure is provided for repairing a dilated valve annulus of an atrioventricular valve, such as a mitral valve. The annuloplasty structure comprises a flexible sleeve and a plurality of anchors. An anchor deployment manipulator is advanced into a lumen of the sleeve, and, from within the lumen, deploys the anchors through a wall of the sleeve and into cardiac tissue, thereby anchoring the sleeve around a portion of the valve annulus. The anchors are typically deployed from a distal end of the manipulator while the distal end is positioned such that a central longitudinal axis through the distal end of the manipulator forms an angle with a surface of the cardiac tissue of between about 20 and 90 degrees, e.g., between about 45 and 90 degrees, e.g., between about 75 and 90 degrees, such as about 90 degrees. Typically, the anchors are deployed from the distal end of the manipulator into the cardiac tissue in a direction parallel to the central longitudinal axis through the distal end of the manipulator.

A multi-component tubular system is provided for accessing a heart of a patient. The system comprises one or more steerable guiding catheters configured for directing the passage of devices therethrough into the heart. The multi-component tubular system is configured to deliver an implant in a desired orientation to an annulus of a cardiac valve of the patient and to facilitate anchoring of the implant to the annulus. For some applications of the present invention, the guiding system is advanced transluminally or transthoracically accessing an atrium of the heart. Typically, the system comprises two or more steerable catheters. A first catheter has a distal portion that is steerable to a first desired spatial orientation. A second catheter is disposed within the first catheter and has a distal portion that is steerable to a second desired spatial orientation.

Typically, the annuloplasty structure comprises a sleeve with an elongated tubular wall and at least one end wall having a surface substantially transverse to a lateral surface of the tubular wall. A method is provided for deploying a first tissue anchor through the surface of the end wall of the sleeve and into annulus tissue and subsequently deploying a second tissue anchor through the tubular wall. The first tissue anchor and the second tissue anchor are both deployed consecutively to extend in a substantially same direction and into a common, substantially planar surface of a valve annulus. That is, the first and second tissue anchors are deployed in succession with no intervening anchor between the anchors, and a distance between the anchors is between 2.5 and 15 mm, e.g., between 2.5 and 9 mm, e.g., 8 mm.

The first and second anchors extend in the substantially same direction despite that the first tissue anchor is deployed through the end wall transverse to the side wall. That is, the first and second anchors extend in the substantially same direction while the first tissue anchor is deployed through the end wall transverse to the side wall.

In such a deployment, a distal end portion of the sleeve between the first and second tissue anchors is formed into a substantial "U"-shaped portion having a concavity facing the tissue of the annulus.

There is therefore provided, in accordance with some applications of the present invention, a method of deploying an annuloplasty structure, the method including:

introducing into a heart atrium, the annuloplasty structure having a sleeve with an elongated tubular side wall and at least one distal end wall having a surface substantially transverse to a lateral surface of the tubular side wall;

deploying a first tissue anchor through the surface of the end wall of the sleeve and into a first portion of annulus tissue; and deploying a second tissue anchor through a portion of the tubular side wall and into a second portion of annulus tissue, such that the first tissue anchor and the second tissue anchor are both deployed consecutively, to extend in a substantially same direction and into a common, substantially planar surface of a valve annulus, the common, substantially planar surface including the first and second portions of the annulus tissue.

In some applications of the present invention, deploying the second tissue anchor includes deploying the second tissue anchor between 2.5 and 15 mm from the first tissue anchor.

In some applications of the present invention, deploying the second tissue anchor includes deploying the second tissue anchor between 2.5 and 9 mm from the first tissue anchor.

In some applications of the present invention, deploying the second tissue anchor through the tubular wall includes deploying the second tissue anchor substantially parallel with respect to the first tissue anchor.

In some applications of the present invention, deploying the second tissue anchor through the tubular wall includes deploying the second tissue anchor between 0 and 45 degrees with respect to the first tissue anchor.

In some applications of the present invention, deploying the second tissue anchor through the tubular wall, includes deploying the second tissue anchor between 0 and 20 degrees with respect to the first tissue anchor.

In some applications of the present invention, deploying the second tissue anchor includes forming a portion of the sleeve between the first and second tissue anchors into a substantially "U"-shaped portion.

In some applications of the present invention, deploying the first anchor includes deploying the first anchor from a distal end of a deployment manipulator through the surface of the end wall of the sleeve into the cardiac tissue, while the distal end of the deployment manipulator is positioned such that a central longitudinal axis through the distal end of the deployment manipulator forms an angle of between 20 and 90 degrees with the distal end wall of the sleeve at a point at which the first anchor penetrates the end wall.

In some applications of the present invention, deploying the first anchor includes deploying the first anchor from a distal end of a deployment manipulator through the surface of the end wall of the sleeve into the cardiac tissue, while the distal end of the deployment manipulator is positioned such that a central longitudinal axis through the distal end of the deployment manipulator forms an angle of between 45 and 90 degrees with the distal end wall of the sleeve at a point at which the first anchor penetrates the end wall.

In some applications of the present invention, deploying the second anchor includes deploying the second anchor from a distal end of a deployment manipulator through the surface of the portion of the tubular wall of the sleeve into the cardiac tissue, while the distal end of the deployment manipulator is positioned such that a central longitudinal axis through the distal end of the deployment manipulator forms an angle of between 20 and 90 degrees with the portion of the tubular wall of the sleeve at a point at which the second anchor penetrates the portion of the tubular wall.

In some applications of the present invention, deploying the second anchor includes deploying the second anchor from a distal end of a deployment manipulator through the surface of the portion of the tubular wall of the sleeve into the cardiac tissue, while the distal end of the deployment manipulator is positioned such that a central longitudinal axis through the distal end of the deployment manipulator forms an angle of between 45 and 90 degrees with the portion of the tubular wall of the sleeve at a point at which the second anchor penetrates the portion of the tubular wall.

In some applications of the present invention, deploying the first anchor includes deploying the first anchor through a channel disposed within a lumen of the sleeve, the channel having a distal end defining an opening through with the first anchor passes, and deploying the first anchor includes sandwiching the surface of the end wall of the sleeve between the distal end of the channel and the first portion of annulus tissue.

In some applications of the present invention, sandwiching includes positioning the distal end of the channel in a manner in which the distal end of the channel is aligned substantially parallel to the planar surface.

In some applications of the present invention, deploying the second anchor includes deploying the second anchor through a channel disposed within a lumen of the sleeve, the channel having a distal end defining an opening through with the second anchor passes, and deploying the second anchor includes sandwiching the portion of the tubular side wall of the sleeve between the distal end of the channel and the second portion of annulus tissue.

In some applications of the present invention, sandwiching includes positioning the distal end of the channel in a manner in which the distal end of the channel is aligned substantially parallel to the planar surface.

In some applications of the present invention, the method further includes, following the deploying the first tissue anchor, flexing the annuloplasty structure while the distal end wall is anchored, to form a portion of the sleeve that is proximal to the distal end into a substantially "U"-shaped portion.

In some applications of the present invention, deploying the second tissue anchor includes forming a portion of the sleeve between the first and second tissue anchors into an arc with a concave surface facing the annulus tissue.

In some applications of the present invention, the method further includes forming a distal portion of the sleeve between the first and second tissue anchors into a shape.

In some applications of the present invention, forming the distal portion of the sleeve into the shape includes forming the distal portion of the sleeve into the shape prior to the deploying of the second anchor by flexing the distal portion of the sleeve.

In some applications of the present invention, forming the distal portion of the sleeve into the shape includes forming the distal portion of the sleeve into the shape responsively to the deploying of the second anchor.

In some applications of the present invention, the annuloplasty structure includes a stiffener configured to bias the annuloplasty structure into the shape.

In some applications of the present invention, forming the distal portion of the sleeve into the shape includes forming the distal portion of the sleeve into a shape in which:

a first part of the lateral surface of the tubular side wall is positioned close to the tissue of the annulus, a second part of the lateral surface of the tubular side wall is disposed opposite the first part of the lateral surface of the tubular side wall and away from the tissue of the annulus, and the second part of the lateral surface of the tubular side wall has a degree of tension that is larger than a degree of tension of the first part of the lateral surface of the tubular side.

In some applications of the present invention, the first part of the lateral surface of the tubular side wall is ruffled and is disposed adjacent the tissue of the annulus.

In some applications of the present invention, forming the distal portion of the sleeve into the shape includes forming the distal portion of the sleeve into a shape having a concavity.

In some applications of the present invention, forming the distal portion of the sleeve into the shape having the concavity includes creating a gap between the distal portion of the sleeve and the annulus tissue, the gap having a longest distance between 0.2 and 7.5 mm.

In some applications of the present invention, forming the portion of the sleeve into the shape having the concavity includes creating a gap between the portion and the annulus tissue, the gap having a longest distance between 0.5 and 3 mm.

In some applications of the present invention, the method further includes, following the deploying the first tissue anchor, flexing the annuloplasty structure while the distal end wall is anchored, to form a concave shape of the structure between (a) a portion of the structure proximal to the distal end wall of the structure, and (b) the annulus, deploying the second tissue anchor includes maintaining the concave shape during the deploying.

In some applications of the present invention, deploying the first tissue anchor and deploying the second tissue anchor includes deploying the first and second tissue anchors from within a lumen of a channel disposed within a lumen of the sleeve while at least a proximal portion of the sleeve is surrounded by a catheter.

In some applications of the present invention, the valve is a mitral valve.

There is also provided, in accordance with some applications of the present invention, a method of repairing a cardiac valve, the method including:

introducing into a heart atrium, a flexible annuloplasty structure having a sleeve with an elongated tubular side wall and at least one distal end wall having a surface substantially transverse to a lateral surface of the tubular side wall;

anchoring the distal end wall of the sleeve to a valve annulus on an atrial surface of the valve by deploying a first tissue anchor;

while the distal end wall is anchored, positioning alongside the valve annulus a portion of the tubular side wall that is proximal to the distal end wall in a manner in which the portion of the tubular side wall assumes a shape in which:

a first part of the lateral surface of the tubular side wall is positioned close to the tissue of the annulus, a second part of the lateral surface of the tubular side wall is disposed opposite the first part of the lateral surface of the tubular side wall and away from the tissue of the annulus, and the second part of the lateral surface of the tubular side wall has a degree of tension that is larger than a degree of tension of the first part of the lateral surface of the tubular side;

anchoring the portion of the tubular side wall to the annulus by deploying a second tissue anchor consecutively to the first tissue anchor; and continuing to position the annuloplasty structure about a circumference of the atrial surface of the annulus while periodically anchoring additional locations of the tubular side wall of the sleeve to the atrial surface of the annulus.

There is additionally provided, in accordance with some applications of the present invention, apparatus for repairing a cardiac valve, the apparatus including:

a flexible annuloplasty structure having a sleeve with an elongated tubular side wall and at least one distal end wall having a surface substantially transverse to a lateral surface of the tubular side wall;

a first tissue anchor passing through the distal end wall of the sleeve; and a second tissue anchor passing through the tubular side wall, the first and second tissue anchors being disposed consecutively and to extend in a substantially same direction.

There is further provided, in accordance with some applications of the present invention, apparatus for repairing a cardiac valve, the apparatus including:

a flexible annuloplasty structure having a sleeve with an elongated tubular side wall and at least one distal end wall having a surface substantially transverse to a lateral surface of the tubular side wall;

a first tissue anchor passing through the distal end wall of the sleeve; and a second tissue anchor passing through the tubular side wall in a manner in which a portion of the tubular side wall that is between the first and second tissue anchors assumes a shape in which:

the portion has a first part of the lateral surface of the tubular side wall and a second part of the lateral surface of the tubular side wall opposite the first part, and the second part of the lateral surface of the tubular side wall has a degree of tension that is larger than a degree of tension of the first part of the lateral surface of the tubular side wall.

There is yet additionally provided, in accordance with some applications of the present invention, a method of repairing a cardiac valve, the method including:

introducing into a heart atrium, an annuloplasty structure having a sleeve with an elongated tubular side wall and at least one distal end wall having a surface substantially transverse to a lateral surface of the tubular side wall;

anchoring, using a first tissue anchor, the distal end wall of the sleeve to a valve annulus on an atrial surface of the valve;

forming a concave shape of a distal portion of the structure between the distal end portion of the structure and the annulus by positioning the tubular side wall in a vicinity of the valve annulus by flexing the annuloplasty structure while the distal end wall is anchored;

anchoring, using a second tissue anchor, a distal portion of the tubular side wall of the sleeve to the annulus, such that when the first tissue anchor and the second tissue anchor are anchored, the concave shape is maintained along the distal portion of the structure; and continuing to position the annuloplasty structure about a circumference of the atrial surface of the annulus while periodically anchoring additional locations of the tubular side wall of the sleeve to the atrial surface of the annulus.

The present invention will be more fully understood from the following detailed description of embodiments thereof, taken together with the drawings, in which:

BRIEF DESCRIPTION OF THE DRAWINGS

FIGS. 4A-G are schematic illustrations of steps in the implantation of an annuloplasty ring structure to repair a mitral valve, in accordance with some applications of the invention;

FIG. 5 is a schematic illustration of a state of a distal portion of a multi-component tubular system within the heart of a subject, in accordance with some applications of the invention;

FIGS. 6A-C are schematic illustrations of a tissue anchor, in accordance with some applications of the present invention.

DETAILED DESCRIPTION OF EMBODIMENTS

Figure 1:
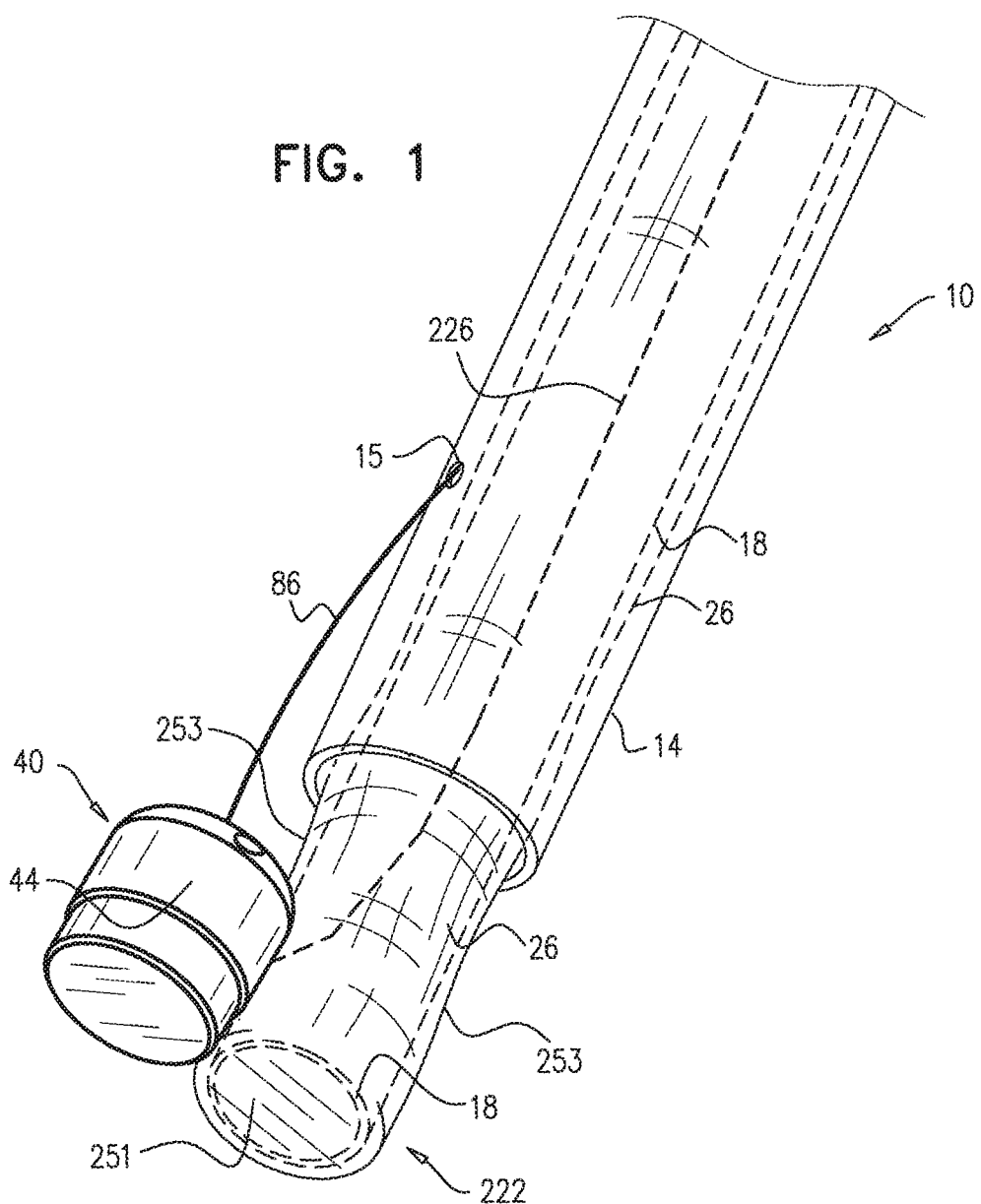
FIG. 1 is a schematic illustration of an annuloplasty ring structure, comprising a sleeve and an adjusting mechanism, in accordance with some applications of the invention.
Figure 2:
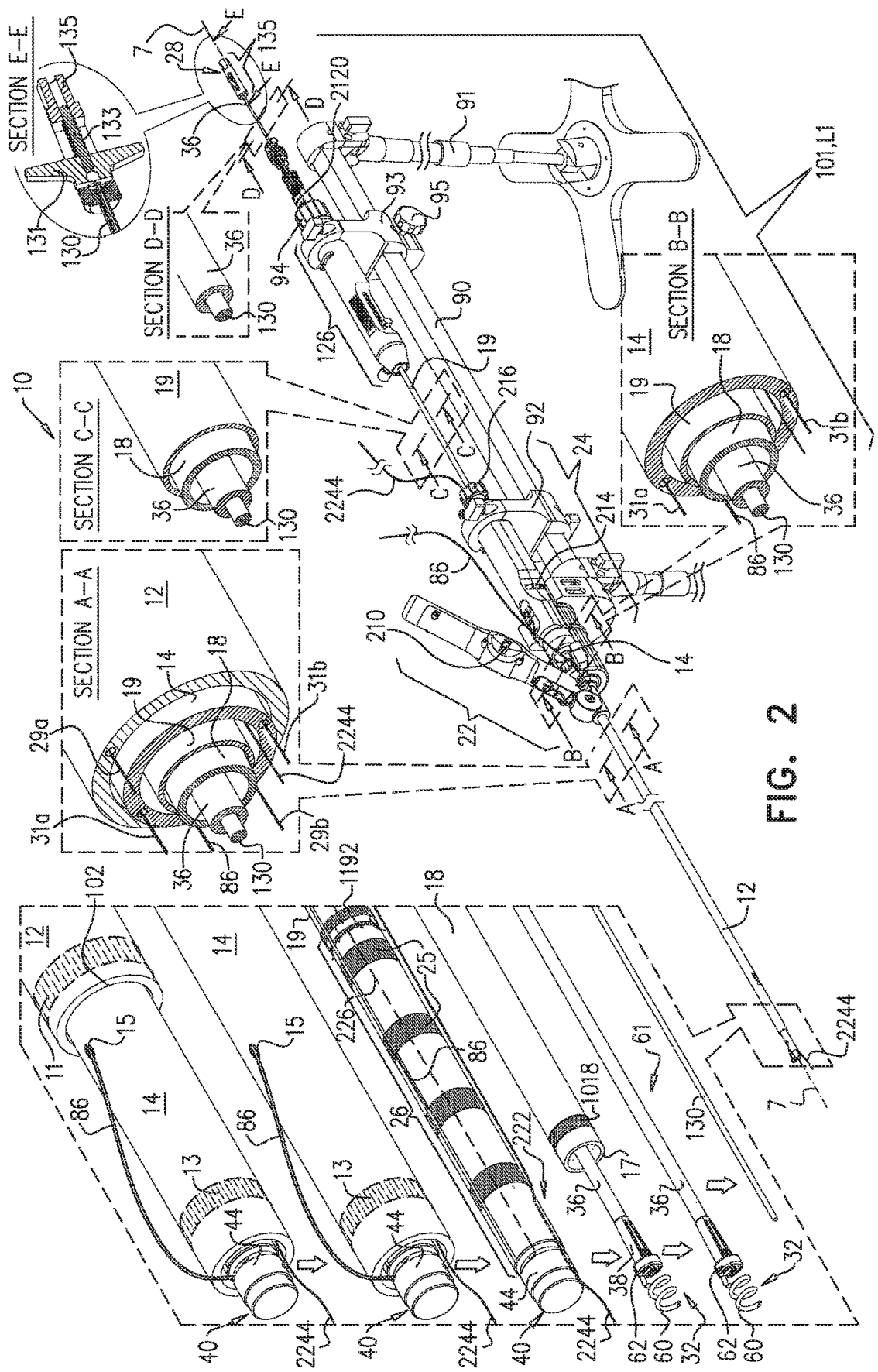
FIG. 2 is a schematic illustration of a multi-component tubular system for delivering and anchoring an implant and for controlling a relative spatial orientation of components of the catheter system, in accordance with some applications of the present invention.

Reference is now made to FIGS. 1-2, which are schematic illustrations of a multi-component tubular system 10 providing one or more rotationally-controlled steering catheters configured for delivering an implant to a heart of a patient, in accordance with some applications of the present invention.

FIG. 1 shows a distal portion of an implant comprises an annuloplasty ring structure 222 (e.g., an annuloplasty band) comprising a flexible sleeve 26 (shown in the exploded view of FIG. 2). Sleeve 26 typically comprises a braided fabric mesh, e.g., comprising DACRON™. Sleeve 26 is typically configured to be placed only partially around a cardiac valve annulus (i.e., to assume a C-shape), and, once anchored in place, to be contracted so as to circumferentially tighten the valve annulus. Alternatively, the ring structure is configured to be placed entirely around the valve annulus.

Sleeve 26 has an elongated lateral tubular side wall 253 and at least one end wall 251 (e.g., a distal end wall) having a surface that is substantially transverse to a lateral surface of tubular wall 253. Typically, end wall 251 defines an end wall of annuloplasty ring structure 222.

In order to tighten the annulus, annuloplasty ring structure 222 comprises a flexible elongated contracting member 226 that extends along sleeve 26. Elongated contracting member 226 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contracting member 226 comprises a braided polyester suture (e.g., Ticron). For some applications, contracting member 226 is coated with polytetrafluoroethylene (PTFE). For some applications, contracting member 226 comprises a plurality of wires that are intertwined to form a rope structure.

Annuloplasty ring structure 222 further comprises an adjustment mechanism 40, which facilitates contracting and expanding of annuloplasty ring structure 222 so as to facilitate adjusting of a perimeter of the annulus and leaflets of the cardiac valve. Adjustment mechanism 40 is described in more detail hereinbelow. Adjustment mechanism 40 comprises a rotatable structure (e.g., a spool, as described hereinbelow) that is disposed within a housing 44. As shown in the enlarged image of FIG. 1, adjustment mechanism 40 is surrounded by a braided mesh and is coupled (e.g., by being sutured or otherwise coupled) to the braided mesh of sleeve 26. For some applications, adjustment mechanism 40 is coupled to an outer, lateral surface of sleeve 26.

Reference is now made to FIG. 2, which shows the concentric relationship between components of tubular system 10 (in an exploded view on the left side of FIG. 2). System 10 comprises an implant-delivery tool. Typically, system 10 comprises a first, outer catheter 12 comprising a sheath configured for advancement through vasculature of a patient. For some applications of the present invention, outer catheter 12 comprises a sheath configured for advancement through a femoral artery toward an interatrial septum of a heart of a patient. A distal steerable end portion of outer catheter 12 is configured to pass through the septum and be oriented in a desired spatial orientation. System 10 comprises a second catheter, or guide catheter 14, comprising a steerable distal end portion. Catheter 14 is configured for advancement through a lumen of outer catheter 12.

A distal end portion of outer catheter 12 is steerable. The distal end portion of outer catheter 12 comprises a pull ring 11 that is coupled to two or more pull wires 29a and 29b, that are disposed within respective secondary lumens within a wall of catheter 12 (as shown in section A-A). As shown in the exploded view, guide catheter 14 is configured to be concentrically disposed within the lumen of catheter 12. As described hereinabove, the distal end portion of guide catheter 14 is steerable. The distal end portion of catheter 14 comprises a pull ring 13 that is coupled to two or more pull wires 31a and 31b, that are disposed within respective secondary lumens within a wall of catheter 14 (as shown in sections A-A and B-B).

Guide catheter 14 is steerable to a desired spatial orientation in order to facilitate advancing and implantation of an implant in a body cavity of the patient.

For applications in which system 10 is used to deliver an implant to the mitral valve of the patient, typically, outer catheter 12 is configured for initial advancement through vasculature of the patient until a distal end 102 of catheter 12 is positioned in the left atrium. The distal steerable end portion of catheter 12 is then steered such that distal end 102 of catheter 12 is positioned in a desired spatial orientation within the left atrium. The steering procedure is typically performed with the aid of imaging, such as fluoroscopy, transesophageal echo, and/or echocardiography. Following the steering of the distal end portion of catheter 12, guide catheter 14 (which houses annuloplasty ring structure 222) is advanced through catheter 12 in order to facilitate delivery and implantation of structure 222 along the annulus of the mitral valve. During the delivery, at least a portion of the steerable distal end portion of catheter 14 is exposed from distal end 102 of catheter 12 and is thus free for steering toward the annulus of the mitral valve, as is described hereinbelow.

During delivery of sleeve 26 to the annulus of the cardiac valve, sleeve 26 and mechanism 40 are disposed within a lumen of catheter 14 and are aligned longitudinally with a longitudinal lumen of catheter 14. Such coupling of mechanism 40 to sleeve 26 allows mechanism 40 to transition from a state in which it is in line with the longitudinal axis of catheter 14 (FIG. 2) to a state in which it is disposed alongside sleeve 26 (FIG. 3C, shown hereinbelow). The positioning of adjustment mechanism 40 alongside a portion of sleeve 26 exposes a driving interface of the rotational structure to be accessed by a rotational tool that is guided toward adjustment mechanism 40 via a guide member 86.

Reference is again made to FIG. 1. A flexible, longitudinal guide member 86 (e.g., a wire) is coupled to a portion of adjustment mechanism 40 (e.g., a portion of the rotatable structure, as described hereinbelow). Guide member 86 is configured to facilitate guiding of a rotational tool via guide member 86 and toward the rotatable structure of adjustment mechanism 40. Typically, the rotational tool is configured to engage the rotatable structure of adjustment mechanism 40 following implantation of sleeve 26 along the annulus of the cardiac valve. Guide member 86 passes from adjustment mechanism 40, alongside a portion of the distal end portion of guide catheter 14, and into a secondary lumen in the wall of guide catheter 14, through an opening 15 in guide catheter 14. Guide member 86 passes through the secondary lumen of guide catheter 14 (as shown in sections A-A and B-B in FIG. 2) and has a proximal end that is accessible from outside the body of the patient. The secondary lumen in the wall of guide catheter 14 facilitates passage of guide member 86 through system 10 without interfering with the other concentrically-disposed elongate tubular members that pass concentrically through the lumen of guide catheter 14.

Reference is again made to FIG. 2. In addition, system 10 comprises a plurality of anchors 32, typically between about 5 and about 20 anchors, such as about 10 or about 16 anchors. Each anchor 32 comprises a tissue coupling element 60 (e.g., a helical tissue coupling element), and a tool-engaging head 62 (e.g., a non-helically-shaped portion), fixed to one end of the tissue coupling element. Only one anchor 32 is shown in FIG. 2 as being reversibly coupled to a deployment element 38 of a rotating anchor driver 36 of an anchor deployment manipulator 61. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus. The insertion of the anchors into the sleeve and deployment of the anchors into cardiac tissue is described in detail hereinbelow.

Typically, but not necessarily, anchors 32 comprise a biocompatible material such as stainless steel 316 LVM. For some applications, anchors 32 comprise nitinol. For some applications, anchors 32 are coated fully or partially with a non-conductive material.

Deployment manipulator 61 comprises anchor driver 36 and deployment element 38. For some applications, deployment manipulator 61 comprises channel 18.

As shown in the exploded view of FIG. 2, sleeve 26 is disposed within a lumen of guide catheter 14. A force is applied to a proximal end of sleeve 26 is by a distal end of a reference-force tube 19. As shown, an implant-decoupling channel 18 is advanceable within a lumen of reference-force tube 19 and through a lumen of sleeve 26. As shown in the enlarged image of FIG. 1, a distal end 17 of implant-decoupling channel 18 is disposed in contact with an inner wall of sleeve 26 at a distal end thereof. Additionally, a distal end portion of channel 18 comprises a radiopaque marker 1018. As shown, tube 19 and sleeve 26 are longitudinally and coaxially disposed with respect to each other.

For some applications, channel 18 is steerable.

Typically, manipulator 61 advances within channel 18. For some applications, system 10 comprises a plurality of anchor drivers 36 of manipulator 61, each driver 36 being coupled to a respective anchor 32. Each driver 36 is advanced within channel 18 in order to advance and implant anchor 32 in tissue. Following implantation of anchor 32, anchor 32 is decoupled from driver 36, as described herein, and driver 36 is removed from within channel 18. Subsequently, a new driver 36 coupled to another anchor 32 is then advanced within channel 18.

As will be described hereinbelow, a first one of anchors 32 is configured to be deployed through end wall 251 of sleeve 26 into cardiac tissue, when sleeve 26 is positioned along the annulus of the valve. Following the deployment of the first tissue anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) reference-force tube 19 is maintained in place in a manner in which a distal end of tube 19 provides a reference force to sleeve 26 in order to facilitate freeing of a successive portion of sleeve 26 from around channel 18. Channel 18 is then positioned at a successive location within the lumen of sleeve 26 while either tube 19 and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers 25, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink.

Typically, at least a portion (e.g., at least three, such as all) of the longitudinal sites are longitudinally spaced at a constant interval. Typically, the longitudinal distance between the distal edges of adjacent/consecutive markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm (If, for example, the distance were 6 mm and the length were 2 mm, the longitudinal gaps between adjacent markers would have lengths of 4 mm.)

Each anchor 32 is coupled to deployment element 38 of anchor driver 36. Anchor driver 36 comprises an elongate tube having at least a flexible distal end portion. The elongate tube of driver 36 extends within a lumen of channel 18, through system 10 toward a proximal end of a proximal handle portion 101 of system 10. The tube of anchor driver 36 provides a lumen for slidable advancement therethrough of an elongate rod 130. Rod 130 facilitates the locking and unlocking of anchor 32 to deployment element 38. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. As is described hereinbelow, the physician releases anchor 32 from deployment element 38 when finger-engager 131 is pulled proximally, thereby pulling rod 130 proximally.

Proximal handle portion 101 is supported by a stand having support legs 91 and a handle-sliding track 90. Handle portion 101 comprises an outer-catheter handle 22, a guide-catheter handle 24, an implant-manipulating handle 126, and anchor-release mechanism 28. Handle 22 is coupled to a proximal end of outer catheter 12. Handle 24 is coupled to a proximal portion of guide catheter 14. Handle 126 is coupled to a proximal portion of reference-force tube 19, and linear movement of handle 126 with respect to handle 24 moves reference-force tube 19 (and thereby typically structure 222) through catheter 14. As described hereinabove, housing 135 of anchor-release mechanism 28 is coupled to a proximal portion of the tube of anchor driver 36. The relative positioning of each of the concentrically-disposed components of system 10 is shown in the exploded view and sections A-A, B-B, C-C, and D-D of FIG. 2.

The stand supporting proximal handle portion 101 may be moved distally and proximally to control a position of the entire multi-component system 10, particularly so as to adjust a distance of distal end 102 of catheter 12 from the interatrial septum. Handle 22 comprises a steering knob 210 that is coupled to steering wires 29a and 29b disposed within respective secondary lumens in the wall of outer catheter 12.

Rotation of knob 210 adjusts a degree of tension of wires 29a and 29b which, in turn, apply a force to pull ring 11 at the distal end portion of outer catheter 12. Such force steers the distal end portion of catheter 12 within the atrium of the heart of the patient in a manner in which the distal end portion of catheter 12 is steered in a first plane that is parallel with the plane of the annulus of the valve (e.g., in a direction from the interatrial septum toward surrounding walls of the atrium). For some applications of the present invention, the distal end portion of catheter 12 may be pre-shaped so as to point downward toward the valve. For other applications, the distal end portion of catheter 12 may be pulled to assume an orientation in which the distal end portion points downward toward the valve. For yet other applications of the present invention, the distal end portion of catheter 12 is not made to point downward toward the valve.

Handle 24 is coupled to track 90 via a first mount 92. Mount 92 is slidable proximally and distally along track 90 in order to control an axial position of guide catheter 14 with respect to outer catheter 12. Mount 92 is slidable via a control knob 216. For example, control knob 216 of mount 92 controls the proximal and distal axial movement of the distal steerable portion of guide catheter 14 with respect to distal end 102 of outer catheter 12. Handle 24 comprises a steering knob 214 that is coupled to steering wires 31a and 31b disposed within respective secondary lumens in the wall of guide catheter 14. Rotation of knob 214 adjusts a degree of tension of wires 31a and 31b which, in turn, apply a force to pull ring 13 at the distal end portion of guide catheter 14. Such force steers the distal end portion of catheter 14 in a second plane within the atrium of the heart of the patient downward and toward the annulus of the cardiac valve. Typically, as described hereinbelow, the distal end portion of guide catheter 14 is steered in the second plane that is substantially perpendicular with respect to the first plane in which the distal end portion of outer catheter 12 is steered.

The combined steering of the respective distal end portions of catheters 12 and 14 directs sleeve 26 down toward the annulus (e.g., via the steering of the distal end portion of catheter 14) and along the perimeter of annulus (e.g., from the posterior section of the valve to the anterior section of the valve, and vice versa), via the steering of the distal end portion of catheter 12.

For some applications, handle 22 may be tilted by the operating physician, in order to further adjust a position of the distal end of catheter 12.

Handle 126 is coupled to track 90 via a second mount 93. Mount 93 is slidable proximally and distally along track 90, in order to control an axial position of reference-force tube 19 and at least a proximal portion of sleeve 26 with respect to guide catheter 14. Mount 93 is slidable via a control knob 95. For example, control knob 95 of mount 93 controls the proximal and distal axial movement of the tube 19 and at least the proximal portion of sleeve 26 with respect to distal end 104 of guide catheter 14. Taken together with the steering of the distal end portion of guide catheter 14, such movement of tube 19 and at least the proximal portion sleeve 26 moves the proximal portion of sleeve 26 toward a desired portion of tissue of the annulus of the valve during deployment of anchors 32 from within the lumen of sleeve 26, as is described hereinbelow.

As is described hereinabove, in order to decouple sleeve 26 from a portion of an outer surface of channel 18, (1) channel 18 is pulled proximally, while (2) reference-force tube 19 is maintained in place. A proximal end of channel 18 is coupled to a knob 94 which adjusts an axial position of channel 18 proximally and distally with respect to reference-force tube 19 and sleeve 26.

Typically, handle portion 101 comprises a release decision facilitation member 127, such as a latch or button, that automatically engages when a given length of sleeve 26 has advanced off channel 18 (e.g., when channel 18 is at a given position with respect to tube 19); typically just before sleeve 26 becomes completely decoupled from channel 18. Engagement of member 127 inhibits proximal movement of channel 18 with respect to tube 19, thereby reducing a likelihood of (e.g., preventing) inadvertent release of sleeve 26. In order to release sleeve 26 (e.g., to decouple channel 18 from the sleeve), the operating physician must disengage member 127, such as by pushing the button, before continuing to withdraw channel 18 proximally. Typically, when engaged, member 127 also inhibits distal movement of channel 18 with respect to tube 19.

Handle portion 101 (comprising handles 22, 24, and 126 and anchor-release mechanism 28) has a length L1 of between 65 and 85 cm, e.g., 76 cm. Typically, as shown, a majority of the body portion of outer-catheter handle 22 is disposed at a non-zero angle with respect to a longitudinal axis 7 of the multiple components of system 10. The steering mechanism provided by handle 22 in order to steer the distal end portion of catheter 12 is disposed within the portion of handle 22 that is disposed at the non-zero angle with respect to axis 7. Handle 22 comprises an in-line tubular portion which is longitudinally disposed in-line along axis 7 and coaxially with respect to handles 24 and 126 and release mechanism 28. The in-line tubular portion is shaped so as to define a lumen for inserting guide catheter 14 therethrough and subsequently into the lumen of outer catheter 12. The in-line tubular portion has a length L24 of between 7 and 11 cm, e.g., 7 cm. Such spatial orientation of the majority of handle 22 at an angle with respect to axis 7 reduces an overall functional length of handle portion 101.

Typically, but not necessarily, a guidewire 2244 extends alongside sleeve 26 to facilitate positioning of sleeve 26 along the annulus.

For some applications, adjustment mechanism 40 is flexibly and/or articulatably coupled to sleeve 26 (e.g., by being coupled to the sleeve via a suture)

Figure 3A:
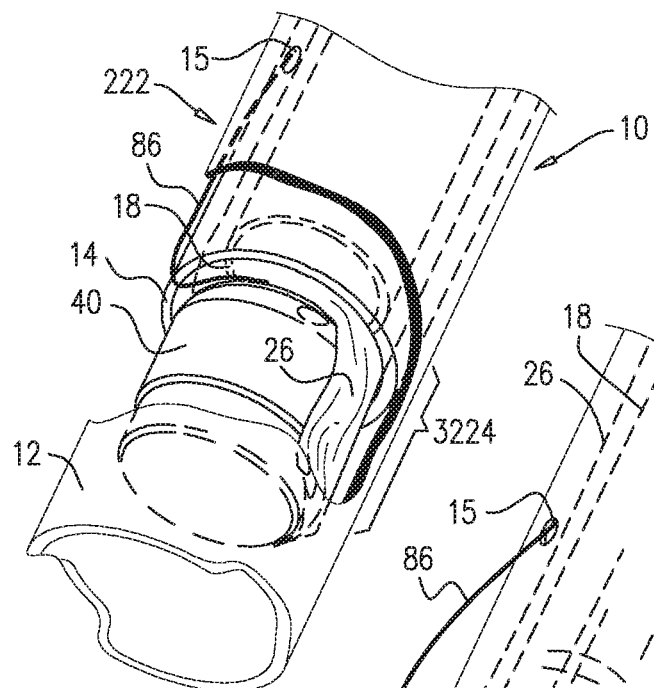
FIGS. 3A-C are schematic illustrations of an annuloplasty ring structure, comprising a sleeve and an adjusting mechanism, in accordance with some applications of the invention.
Figure 3B:
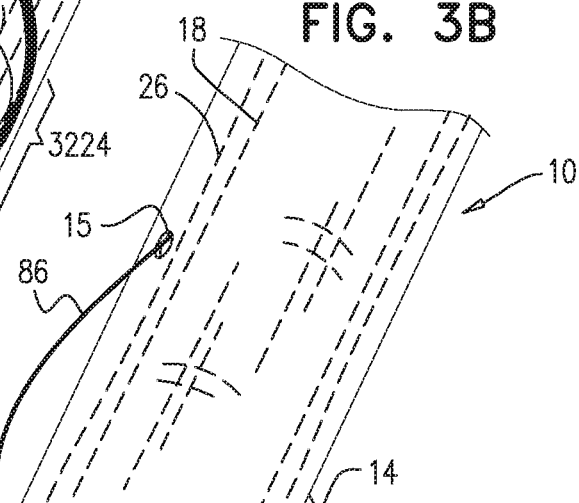
Figure 3C:
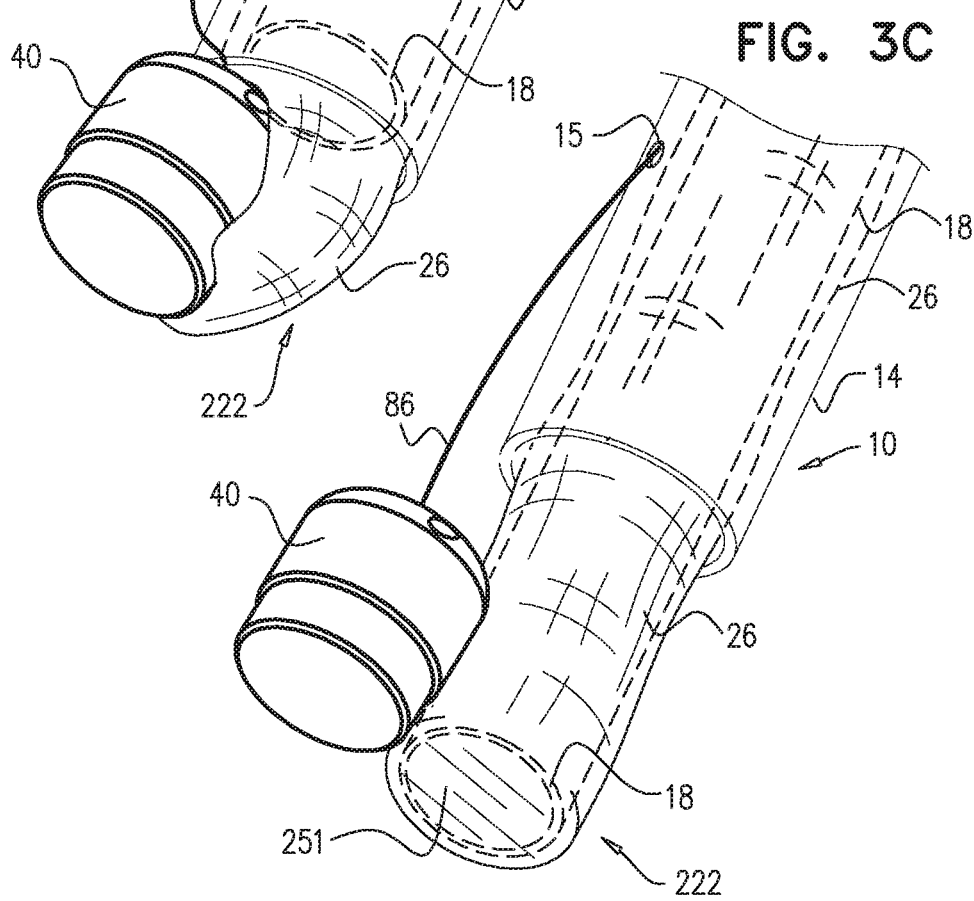

Reference is now made to FIGS. 3A-C, which are schematic illustrations of annuloplasty ring structure 222, comprising sleeve 26 and adjustment mechanism 40, in accordance with some applications of the invention. For some applications it is advantageous to (1) advance the structure to the mitral valve while mechanism 40 is disposed on the longitudinal axis of sleeve 26 (e.g., collinearly with the sleeve), so as to maintain a small cross-sectional diameter of the structure for transluminal delivery; and (2) to subsequently move mechanism 40 away from the longitudinal axis, e.g., so as to allow end wall 251 of the sleeve to be placed against the annulus, and/or so as to allow an anchor to be driven through the end wall of the sleeve. Structure 222 facilitates this technique by mechanism 40 being flexibly and/or articulatably coupled to sleeve 26.

Adjustment mechanism 40 of structure 222 is coupled to the lateral wall of sleeve 26 of structure 222, as shown in FIG. 3C. For delivery of structure 222, channel 18 is not disposed throughout the entire lumen of sleeve 26. Rather, a region 3224 (e.g., a distal region) of sleeve 26 is provided in which channel 18 is not disposed in the lumen of the sleeve, and mechanism 40 is pressed laterally into region 3224, such that the sleeve is compressed at region 3224, and mechanism 40 is disposed on the longitudinal axis of the sleeve (e.g., collinearly with the sleeve). Typically, region 3224 includes end wall 251 of sleeve 26. It is to be noted, however, that region 3224 may be provided at another position along the longitudinal axis of sleeve 26. Typically, mechanism 40 is fixedly coupled to the lateral wall of sleeve 26 at region 3224. In this state, structure 222 is disposed within catheter 14 for delivery.

Structure 222 is advanced out of catheter 14. Once at least adjustment mechanism 40 and/or structure/portion 222 is exposed from catheter 14, the adjustment mechanism moves (e.g., translates) away from the longitudinal axis of sleeve 26 (e.g., laterally), typically by channel 18 being moved distally such that it pushes laterally the portion of the lateral wall of the sleeve to which the adjustment mechanism is coupled (FIG. 3B). FIG. 3C shows channel 18 having been moved all the way to distal end 251 of sleeve 26, and mechanism 40 having been moved away from the longitudinal axis of the sleeve, so as to allow the distal end of the sleeve to be placed against the annulus, and/or so as to allow an anchor to be driven through the distal end wall of the sleeve.

Reference is made to FIGS. 4A-G, which are schematic illustrations of steps in the implantation of an annuloplasty ring structure to repair a mitral valve, in accordance with some applications of the invention. This procedure is one exemplary procedure that can be performed using system 10.

Annuloplasty ring structure 222 is used to repair a dilated valve annulus of an atrioventricular valve, such as mitral valve 230. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises flexible sleeve 26 and a plurality of anchors 32. Anchor deployment manipulator 61 is advanced into a lumen of sleeve 26, and, from within the lumen, deploys the anchors through a wall of the sleeve and into cardiac tissue, thereby anchoring the sleeve around a portion of the valve annulus. For some applications, annuloplasty ring structure 222 is implemented using techniques described in U.S. application Ser. No. 12/437,103, filed May 7, 2009 which published as US 2010/0286767, and which issued as U.S. Pat. No. 8,715,342, and/or U.S. application Ser. No. 12/689,635, filed Jan. 19, 2010 which published as US 2010/0280604, and which issued as U.S. Pat. No. 8,545,553, both of which are assigned to the assignee of the present application and are incorporated herein by reference. As described hereinabove, annuloplasty ring structure 222 comprises adjustment mechanism 40. The adjustment mechanism comprises a rotatable structure, such as a spool, arranged such that rotation of the rotatable structure contracts the implant structure. The implant further comprises a longitudinal member, such as a wire, which is coupled to the adjustment mechanism. A rotation tool is provided for rotating the rotatable structure. The tool is configured to be guided along (e.g., over, alongside, or through) the longitudinal member, to engage the rotatable structure, and to rotate the rotatable structure in response to a rotational force applied to the tool.

The procedure typically begins by advancing a semi-rigid guidewire into a right atrium 220 of the patient. The procedure is typically performed with the aid of imaging, such as fluoroscopy, transesophageal echo, and/or echocardiography.

The guidewire provides a guide for the subsequent advancement of outer catheter 12 therealong and into the right atrium. Once a distal portion of catheter 12 has entered the right atrium, the guidewire is retracted from the patient's body. Catheter 12 typically comprises a 14-24 F sheath, although the size may be selected as appropriate for a given patient. Catheter 12 is advanced through vasculature into the right atrium using a suitable point of origin typically determined for a given patient. For example:

catheter 12 may be introduced into the femoral vein of the patient, through an inferior vena cava 223, into right atrium 220, and into a left atrium 224 transseptally, typically through the fossa ovalis;

catheter 12 may be introduced into the basilic vein, through the subclavian vein to the superior vena cava, into right atrium 220, and into left atrium 224 trans septally, typically through the fossa ovalis; or catheter 12 may be introduced into the external jugular vein, through the subclavian vein to the superior vena cava, into right atrium 220, and into left atrium 224 transseptally, typically through the fossa ovalis.

For some applications of the present invention, catheter 12 is advanced through inferior vena cava 223 of the patient (as shown) and into right atrium 220 using a suitable point of origin typically determined for a given patient.

Catheter 12 is advanced distally until the sheath reaches the interatrial septum, and the guidewire is withdrawn.

A resilient needle and a dilator are advanced through catheter 12 and into the heart. In order to advance catheter 12 transseptally into left atrium 224, the dilator is advanced to the septum, and the needle is pushed from within the dilator and is allowed to puncture the septum to create an opening that facilitates passage of the dilator and subsequently catheter 12 therethrough and into left atrium 224. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum. A distal-most end 102 of catheter 12 is tapered so as to facilitate passage of the distal portion of catheter 12 through the opening in the septum.

The advancement of catheter 12 through the septum and into the left atrium is followed by the extraction of the dilator and the needle from within catheter 12. Once the distal portion of catheter 12 is disposed within atrium 224, the steerable distal end portion of catheter 12 (which includes at least a portion of a bending section 1203) is steered in a first plane that is parallel to a plane of the annulus of mitral valve 230. Such steering moves the distal end portion of catheter 12 in a direction from the interatrial septum toward surrounding walls of the atrium, as indicated by the arrow in atrium 224. The steering of the distal portion of catheter 12 is performed via steering knob 210 of handle 22 in handle portion 101 (in FIG. 2).

Figure 4A:
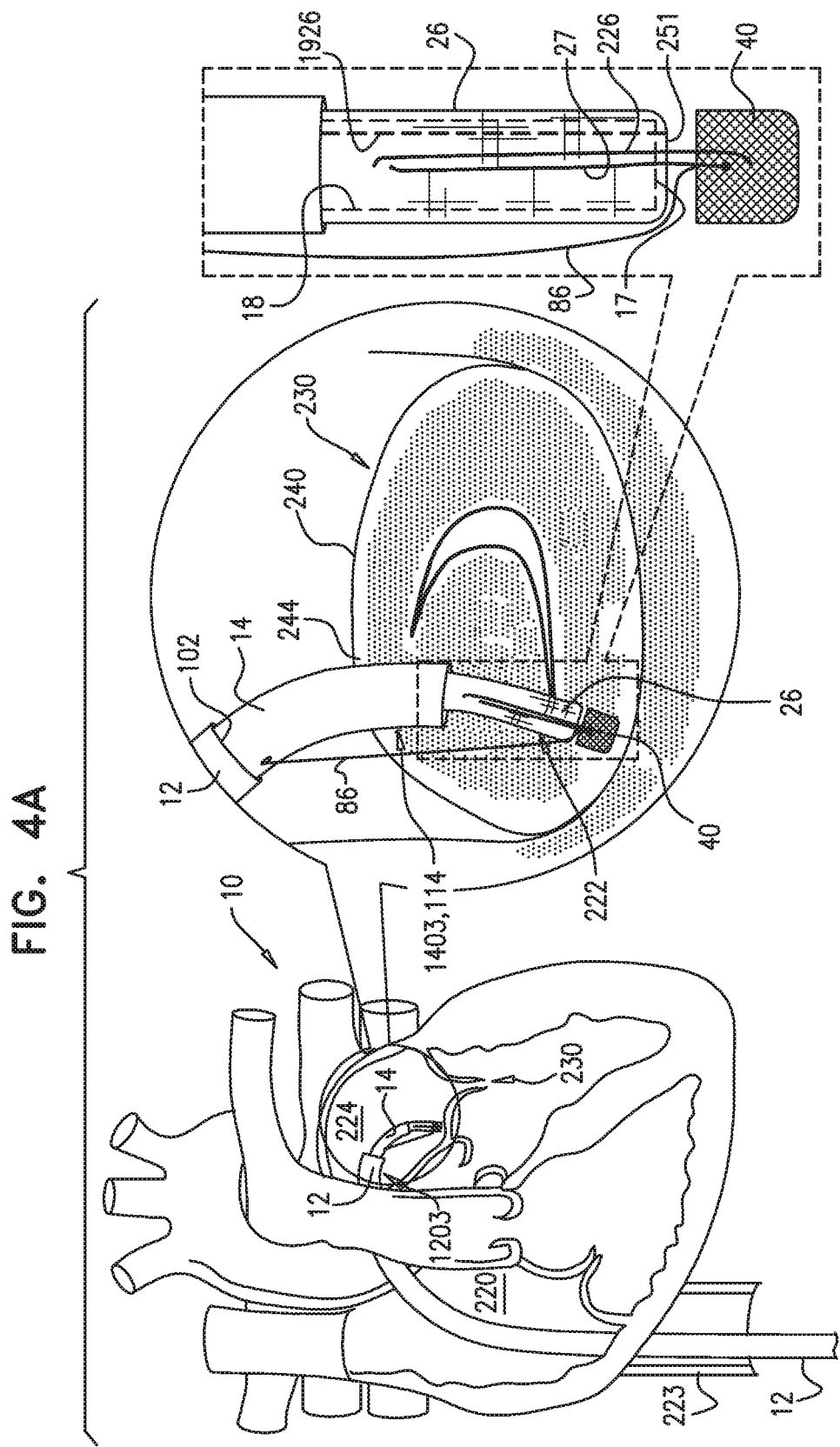

As shown in FIG. 4A, annuloplasty ring structure 222 with channel 18 housing the anchor deployment manipulator 61 (not shown) therein is advanced through guide catheter 14, which is in turn, advanced through catheter 12 into left atrium 224. An exposed distal end portion 114 of catheter 14 extends beyond distal end 102 of catheter 12. Exposed distal end portion 114 is then (1) steered toward the annulus of valve 230 along a plane that is perpendicular with respect to the steering plane of catheter 12 and that is perpendicular with respect to valve 230, and is (2) bent, via a bending section 1403 toward valve 230. The steering of the distal portion of catheter 14 is performed via steering knob 214 of handle 24 in handle portion 101 (in FIG. 2).

FIG. 4A shows annuloplasty ring structure 222, comprising sleeve 26 and adjustment mechanism 40, having been advanced, via catheter 14, to a mitral valve 230. As shown in FIG. 4A, and as described hereinabove, during advancement of structure 222, adjustment mechanism 40 is disposed distal to (i.e., in front of) sleeve 26. In this way, adjustment mechanism 40 is disposed on the longitudinal axis of sleeve 26 (e.g., collinearly with the sleeve), so as to advantageously maintain a small cross-sectional diameter of the implant for transluminal delivery. Mechanism 40 is typically coupled to sleeve 26 via one or more connectors 27, such as sutures, which provide flexible and/or articulated coupling. A proximal end of connector 27 is disposed proximally to mechanism 40 (e.g., by being fixed to a portion of sleeve 26 proximal to mechanism 40 or by being accessible outside the body of the patient). A distal end of connector 27 is coupled (e.g., by being fixedly coupled by a knot or other mechanical coupling) to mechanism 40. Guide member 86, described hereinabove, typically extends distally from catheter 14, between end wall 251 of sleeve 26 and adjustment mechanism 40, and there is coupled to the adjustment mechanism. For some applications it is advantageous to (1) advance the structure to the mitral valve while mechanism 40 is disposed on the longitudinal axis of sleeve 26 (e.g., collinearly with the sleeve), so as to maintain a small cross-sectional diameter of the structure for transluminal delivery; and (2) to subsequently move mechanism 40 away from the longitudinal axis, e.g., so as to allow end wall 251 of the sleeve to be placed against the annulus, and/or so as to allow an anchor to be driven through the end wall of the sleeve. Connectors 27 facilitate this technique by making mechanism 40 flexibly and/or articulatably coupled to sleeve 26. For some applications, connectors 27 are tensioned or relaxed to move mechanism 40 with respect to sleeve 26 to reposition mechanism 40. For some applications, guide member 86 is tensioned or relaxed in order to reposition mechanism 40.

For some applications, mechanism 40 is coupled to sleeve 26 in a manner as described hereinabove with reference to FIGS. 1 and 3A-C.

Figure 4B:
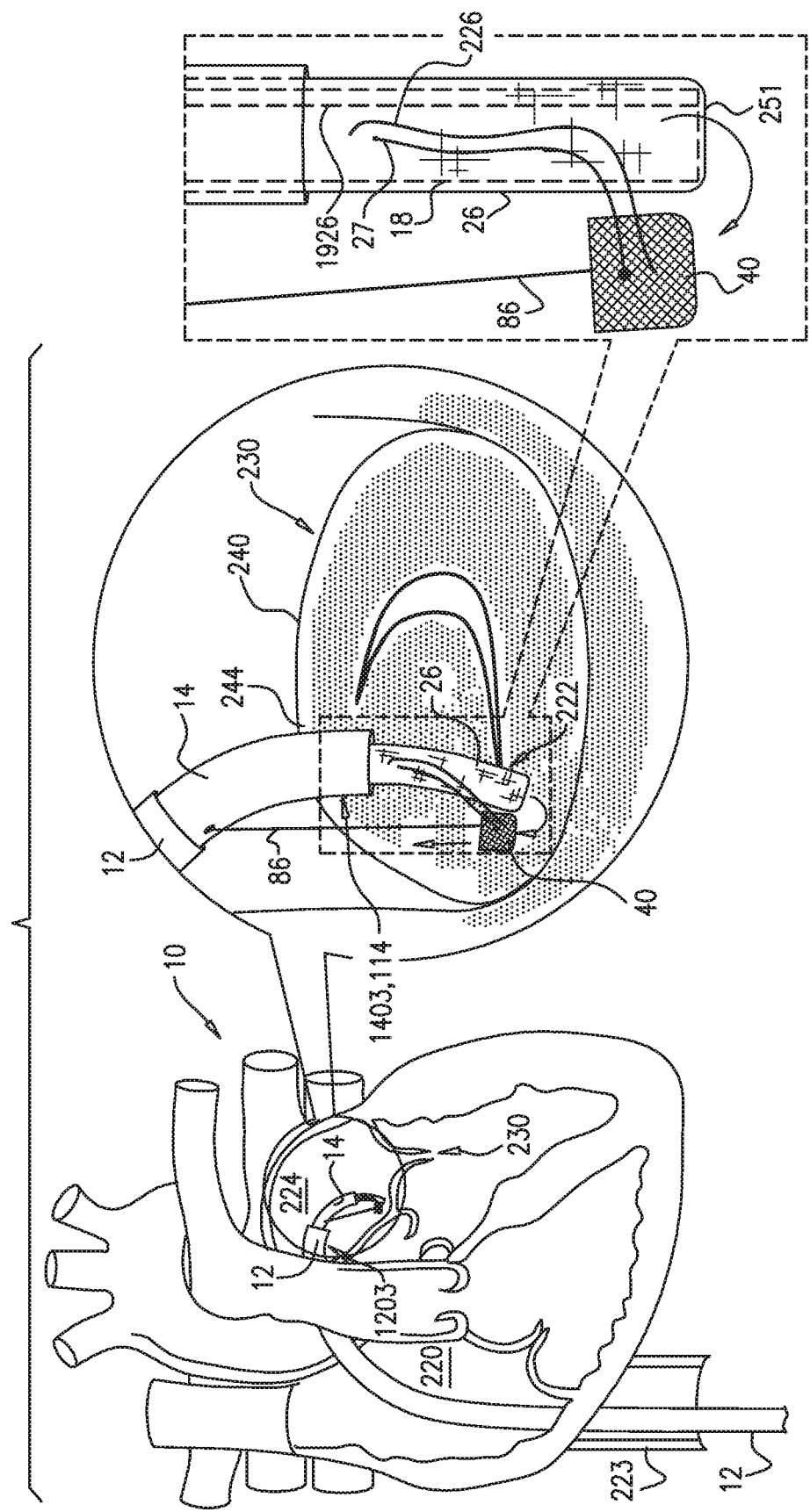

Subsequent to exposure of at least adjustment mechanism 40 (and typically at least end wall 251 of sleeve 26) from catheter 14, the adjustment mechanism is moved away from end wall 251. Typically, this is achieved by guide member 86 being proximally such that mechanism 40 moves (e.g., translates, deflects, and/or rotates) away from the longitudinal axis of the sleeve, typically to become disposed laterally from sleeve 26. FIG. 4B shows mechanism 40 having translated to such a position. The movement of mechanism 40 away from end wall 251 of sleeve 26 advantageously allows end wall 251 of sleeve 26 to be placed against an atrial surface of an annulus 240, and a first one of anchors 32 to be driven through end wall 251 of the sleeve and into the annulus (FIG. 4C).

Figure 4C:
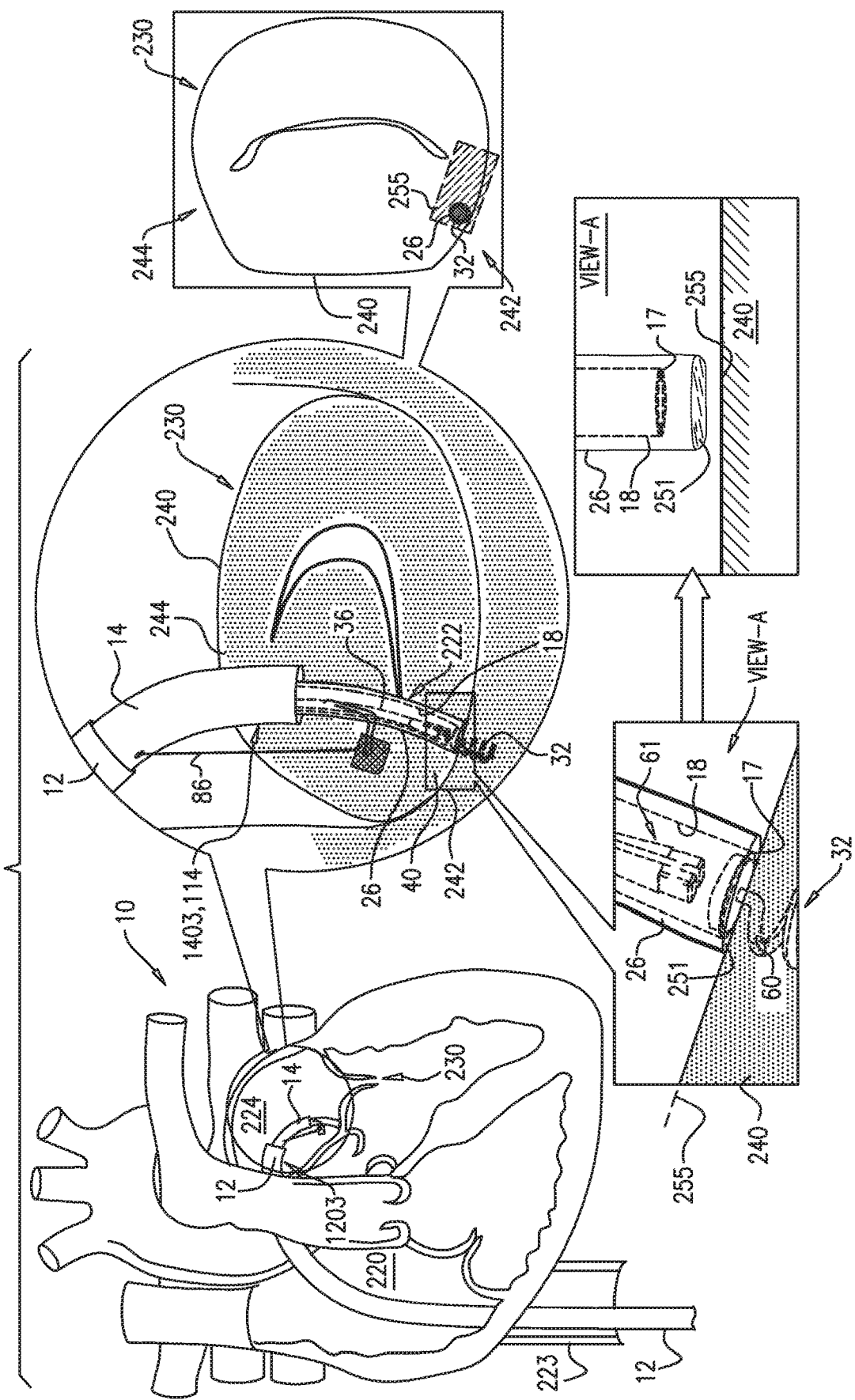

As shown in FIG. 4C, end wall 251 of sleeve 26 is positioned in a vicinity of a left fibrous trigone 242 of an annulus 240 of mitral valve 230. (It is noted that for clarity of illustration, distal end wall 251 of sleeve 26 is shown schematically in the cross-sectional view of the heart, although left trigone 242 is in reality not located in the shown cross-sectional plane, but rather out of the page closer to the viewer.) Alternatively, the distal end of sleeve 26 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site near the selected trigone, deployment manipulator 61 deploys the first one of anchors 32 through the wall of sleeve 26 (by penetrating and passing through the wall of the sleeve in a direction in a direction parallel to a central longitudinal of deployment manipulator 61, or anchor driver 36, through the distal end of channel 18, and/or parallel to central longitudinal axis of tissue coupling element 60 of anchor 32) into cardiac tissue near the trigone. Following the deployment of anchor 32 in the cardiac tissue, deployment element 38 is decoupled from anchor 32.

Anchors 32 are typically deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the atrial surface of the cardiac tissue in a direction parallel to the central longitudinal axis through the distal end of manipulator 61. Such an angle is typically provided and/or maintained by channel 18 being more rigid than sleeve 26. Distal end 17 of channel 18 is typically brought close to the surface of the cardiac tissue (and the wall of sleeve 26 that is disposed against the surface of the cardiac tissue), such that little of each anchor 32 is exposed from channel 18 before penetrating the sleeve and the tissue. For example, distal end 17 of channel 18 may be placed (e.g., pushed) against the wall of the sleeve, sandwiching the sleeve against the cardiac tissue.

For some applications, such placement of distal end 17 of channel 18 against the cardiac tissue (via the wall of the sleeve), stabilizes the distal end during deployment and anchoring of each anchor 32, and thereby facilitates anchoring. For some applications, pushing of distal end 17 against the cardiac tissue (via the wall of the sleeve) temporarily deforms the cardiac tissue at the site of contact. This deformation may facilitate identification of the site of contact using imaging techniques (e.g., by identifying a deformation in the border between cardiac tissue and blood), and thereby may facilitate correct positioning of the anchor.

That is, the entire circular surface of distal end 17 of channel 18 is disposed in contact with the wall of sleeve 26 that is disposed against the surface of the cardiac tissue. As shown, distal end 17 is the lower-most circular tip of channel 18 and defines a distal opening of channel 18. In the configuration in which channel 18 is positioned in order to sandwich the portion of sleeve 26, the distal end 17 is disposed in parallel with a planar surface 255 of the tissue of annulus 240.

View-A provides an exploded view of components of system 10 isolated in relative spatial orientation. View-A shows (1) sleeve 26 and distal end wall 251, (2) channel 18 and distal end 17 thereof, and (3) tissue of annulus 240 at planar surface 255. Deployment manipulator 61 and anchor 32 are not shown in View-A for clarity of illustration. View-A shows the alignment of channel 18, specifically distal end 17 thereof, with respect to distal end wall 251 of sleeve 26, and tissue of annulus 240 at planar surface 255. That is, in such an alignment, distal end 17 is aligned substantially in parallel with respect to distal end wall 251 of sleeve 26, and tissue of annulus 240 at planar surface 255.

Also, for clarity in View-A, distal end 17 of channel 18 is distanced from end wall 251, which is distanced from the tissue of annulus 240. It is to be noted that this distancing is shown by way of illustration only, and that during the procedure of implanting anchor 32 into tissue and through wall 251, distal end 17 of channel contacts wall 251, which contacts tissue of annulus 240. That is, channel 18 is pushed against wall 251 such that distal end 17 of channel sandwiches wall 251 between distal end 17 and the tissue of annulus 240.

For some applications of the present invention, anchors 32 may be deployed from a lateral portion of manipulator 61.

As shown in the enlarged image of FIG. 4C, end wall 251 aligns against the tissue of annulus 240 in a manner in which a surface of end wall 251 is disposed in parallel with a planar surface 255 of the tissue of annulus 240. Additionally, distal end 17 of implant-decoupling channel 18 flattens end wall 251 against the tissue of annulus 240 in a manner in which channel 18 sandwiches end wall 251 between (1) distal end 17 of implant-decoupling channel, and (2) the portion of the tissue of annulus 240 at planar surface 255 into which a first one of anchors 32 is implanted. In such a manner, end wall 251 lies flat against the tissue of annulus 240 in parallel with planar surface 255, while at least a distal portion of tubular side wall 253 is disposed substantially perpendicularly with respect to the portion of the tissue of annulus 240 at planar surface 255 into which the first one of anchors 32 is implanted.

As shown, anchor 32 is implanted using channel 18 and manipulator 61 contained within sleeve 26 of annuloplasty structure 222 while at least a portion of annuloplasty structure 222 is contained within surrounding catheter 14.

Reference is now made to FIGS. 4C and 2. Following the deployment of the first tissue anchor, a distal portion of sleeve 26 is decoupled from a portion of implant-decoupling channel 18. In order to decouple the portion of sleeve 26 from outer surface of channel 18, (1) channel 18 is pulled proximally, while (2) reference-force tube 19 is maintained in place in a manner in which a distal end of tube 19 provides a reference force to sleeve 26 in order to facilitate retraction freeing of a successive portion of sleeve 26 from around channel 18. In order to decouple sleeve 26 from the outer surface of channel 18, (1) channel 18 is pulled proximally, while (2) reference-force tube 19 is maintained in place. An indicator 2120 on handle 126 provides an indication of how much channel 18 is withdrawn from within sleeve 26 (i.e., how much the delivery tool is decoupled from sleeve 26, and how much the sleeve has advanced off channel 18 and against tissue). A proximal end of channel 18 is coupled to a knob 94 (FIG. 2) which adjusts an axial position of channel 18 proximally and distally with respect to reference-force tube 19 and sleeve 26. As shown in FIG. 4D, deployment manipulator 61 is repositioned along annulus 240 to another site selected for deployment of a second one of anchors 32.

Reference is now made to FIGS. 2 and 4D. Such repositioning of manipulator 61 is accomplished by:

(1) the steering of the distal end portion of catheter 12 (e.g., by steering knob 210 of handle 22) in the first plane that is parallel with respect to annulus 240 of valve 230 to a desired spatial orientation and in a manner which bends bending section 1203 of catheter 12, (2) the steering of the distal end portion of portion of catheter 14 (e.g., by steering knob 214 of handle 24) in the second plane that is perpendicular with respect to annulus 240 of valve 230 to a desired spatial orientation, and in a manner which bends bending section 1405 of catheter 14 (specifically bending section 1403), (3) by axially moving catheter 14 with respect to catheter 12 via knob 216, (4) by axially moving the stand supporting handles 22 and 24 to move both catheters 12 and 14, (5) by moving tube 19 and sleeve 26 axially by sliding mount 93 along track 90 via knob 95, and/or (6) by moving channel 18 relative to tube 19 by actuating knob 94.

As shown in the enlarged in-phantom image to the right, during repositioning of manipulator 61 (i.e., during flexing of the annuloplasty structure 222/sleeve 26 while distal end wall 251 is anchored), a generally-triangular shape is formed between: (1) guide member 86, (2) a distal end portion 257 of side wall 253 sleeve 26 (i.e., the portion of the sleeve that is proximal to end wall 251), and (3) channel 18 surrounded partially by catheter 14. It is to be noted that the illustrated triangle is shown in phantom to indicate the relative triangular orientation of the three components, and that the illustrated triangle is not a part of the apparatus shown.

Typically, the first tissue anchor is deployed most distally in the sleeve (generally at or within a few millimeters of the distal tip of the sleeve), and each subsequent anchor is deployed more proximally, such that the sleeve is gradually decoupled from channel 18 of deployment manipulator 61 in a distal direction during the anchoring procedure (i.e., channel 18 is withdrawn from within sleeve 26, and handle 126 is moved distally so as to retract the tool to make the successive proximal portion sleeve 26 ready for implantation of a subsequent anchor). The already-deployed first one of anchors 32 holds the anchored end of sleeve 26 in place, so that the sleeve is drawn from the site of the first tissue anchor towards the site of the second tissue anchor. As sleeve 26 is drawn and decoupled from channel 18, distal portion 257 of sleeve 26 (i.e., the portion of the sleeve that is proximal to end wall 251) is positioned in a vicinity of tissue of annulus 240.

Typically, as sleeve 26 is decoupled from channel 18, deployment manipulator 61 is moved generally laterally along planar surface 255 of the cardiac tissue, as shown in FIG. 4D in a manner which exposes distal portion 257 of sleeve 26 (i.e., the portion of the sleeve that is proximal to end wall 251) and flexes portion 257 to create a generally "U"-shaped portion (i.e., a portion having a concavity with respect to tissue of annulus 240 at planar surface 255). Forming portion 257 of sleeve 26 into the generally "U"-shaped portion (i.e., a portion having a concavity with respect to tissue of annulus 240 at planar surface 255) comprises creating a gap between portion 257 and the tissue of annulus 240 at planar surface 255, the gap having a longest distance D1 between 0.2 and 7.5 mm, e.g., 0.5 and 3 mm. Additionally, such forming of portion 257 is accomplished by flexing portion 257 while end wall 251 is anchored to the tissue of annulus 240. Typically, the gap is formed between (1) the tissue of annulus 240 at planar surface 255, and (2) a first part 258 of the lateral surface distal end portion of side wall 253 (i.e., at portion 257). First part 258 is disposed close to the tissue of annulus 240.

Typically, the "U"-shape differs from the natural shape of annulus 240, as it is distanced from the tissue.

Distal end portion 257 has a tubular, lateral surface. Portion 257 is formed into the generally "U"-shaped portion (i.e., a portion having a concavity with respect to tissue of annulus 240 at planar surface 255) such that first part 258 of the lateral surface of the distal end portion 257 of side wall 253 is formed into a concave surface with respect to the tissue of annulus 240. For some applications, when portion 257 is formed into the generally "U"-shaped portion (i.e., a portion having a concavity with respect to tissue of annulus 240 at planar surface 255), a shape is achieve in which: (1) first part 258, that is concave and disposed closer to the tissue of annulus 240, while (2) a second part 259 of the lateral surface of portion 257 of side wall 253 (i.e., opposite first part 258 and father away from the tissue of annulus 240) is more tensioned and less curved than first part 258. That is, first part 258 has (1) a greater degree of curvature than second part 259, (2) a smaller degree of tension than second part 259, and (3) a smaller radius of curvature than second part 259. Additionally, second part 259 has (1) a smaller degree of curvature than first part 258, (2) a greater degree of tension than first part 258, and (3) a larger radius of curvature than first part 259.

For some applications, part 258 is crimped or ruffled when portion 257 assumes the general "U"-shape.

For some applications, the shape of portion 257 is actively formed by flexing sleeve 26 by deployment manipulator 61. For other applications, the shape of portion 257 is passively assumed during the decoupling of portion 257 of sleeve 26 from channel 18, positioning of portion 257 in a vicinity of tissue of the annulus, and subsequently, anchoring side wall 253 to annulus 240 using the second tissue anchor.

FIG. 4D shows distal portion 257 of sleeve 26 (i.e., the portion of the sleeve that is proximal to end wall 251) having been decoupled from a portion of channel 18 by retracting channel 18 proximally. Depending on the tension applied between the first and second tissue anchor sites, the portion of sleeve 26 therebetween may remain tubular in shape, or may become flattened, which may help reduce any interference of the ring with blood flow.

FIG. 4E shows a second tissue anchor 32 (shown as a second tissue anchor 32b) being deployed through a portion of lateral side wall 253 of sleeve 26. As shown, the first one of anchors 32 deployed through end wall 251 is labeled as anchor 32a. Deployment manipulator 61 deploys the second tissue anchor by penetrating and passing through the wall of sleeve 26 into cardiac tissue at the second site.

As shown, anchor 32b is implanted using channel 18 and manipulator 61 contained within sleeve 26 of annuloplasty structure 222 while at least a portion of annuloplasty structure 222 is contained within surrounding catheter 14.

As described hereinabove, anchors 32a and 32b are each deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the atrial surface of the cardiac tissue in a direction parallel to the central longitudinal axis through the distal end of manipulator 61. Such an angle is typically provided and/or maintained by channel 18 being more rigid than sleeve 26. Distal end 17 of channel 18 is typically brought close to the surface of the cardiac tissue (and the wall of sleeve 26 that is disposed against the surface of the cardiac tissue), such that little of anchor 32b is exposed from channel 18 before penetrating the sleeve and the tissue. For example, distal end 17 of channel 18 may be placed (e.g., pushed) against the wall of the sleeve, sandwiching the sleeve against the cardiac tissue. Reference is made to FIGS. 4D-E. FIG. 4D shows channel 18 of deployment manipulator 61 positioned in alignment with a portion of tubular side wall 253 prior to implantation of the next, consecutive anchor 32 (i.e., 32b, as shown in FIG. 4E). 4D shows a View-B, which provides an exploded view of components of system 10 isolated in relative spatial orientation. View-B shows (1) sleeve 26 and a portion of tubular side wall 253, (2) channel 18 and distal end 17 thereof, and (3) tissue of annulus 240 at planar surface 255. Deployment manipulator 61 and anchor 32 are not shown in View-B for clarity of illustration. View-B shows the alignment of channel 18, specifically distal end 17 thereof, with respect to the portion of tubular side wall 253 of sleeve 26, and tissue of annulus 240 at planar surface 255. That is, in such an alignment, distal end 17 is aligned substantially in parallel with respect to the portion of tubular side wall 253 of sleeve 26, and tissue of annulus 240 at planar surface 255.

Also, for clarity in View-B, distal end 17 of channel 18 is distanced from the portion of tubular side wall 253, which is distanced from the tissue of annulus 240. It is to be noted that this distancing is shown by way of illustration only, and that during the procedure of implanting anchor 32 into tissue and through the portion of tubular side wall 253, distal end 17 of channel contacts the portion of tubular side wall 253, which contacts tissue of annulus 240. That is, channel 18 is pushed against the portion of tubular side wall 253 such that distal end 17 of channel sandwiches the portion of tubular side wall 253 between distal end 17 and the tissue of annulus 240.

As shown in the enlarged image of FIG. 4E, a portion of side wall 253 aligns against the tissue of annulus 240 in a manner in which a surface of the portion of side wall 253 is disposed in parallel with planar surface 255 of the surface of the tissue of annulus 240. Additionally, distal end 17 of implant-decoupling channel 18 flattens the portion of side wall 253 against the tissue of annulus 240 in a manner in which channel 18 sandwiches the portion of side wall 253 between (1) distal end 17 of implant-decoupling channel, and (2) the portion of the tissue of annulus 240 at planar surface 255 into which second tissue anchor 32b is implanted. In such a manner, the portion of side wall 253 lies flat against the tissue of annulus 240 in parallel with planar surface 255, while the remaining portion of tubular side wall 253 is disposed substantially perpendicularly with respect to the portion of the tissue of annulus 240 at planar surface 255 into which second tissue anchor 32b is implanted.

As shown in the right-most, above-view of FIG. 4E, first and second tissue anchors 32a and 32b extend in a substantially same direction and into a common, substantially planar surface 255 of a valve annulus. First and second anchors 32a and 32b extend in the substantially same direction despite that first tissue anchor 32a is deployed through end wall 251 transverse to side wall 253. That is, first and second anchors 32a and 32b extend in the substantially same direction while first tissue anchor 32a is deployed through end wall 251 transverse to side wall 253.

As shown in the bottom-left enlarged image, anchors 32a and 32b are deployed consecutively (i.e., in succession with no intervening anchor between anchors 32a and 32b) and extend in a substantially same direction. For example, anchors 32a and 32b are substantially parallel (e.g., parallel) with respect to each other. For some applications, anchors 32a and 32b are disposed with respect to each other at an angle of between 0 and 45 degrees, e.g., between 0 and 30 degrees, e.g., between 0 and 20 degrees. For some applications, first and second tissue anchors 32a and 32b, respectively, are deployed consecutively. That is, first and second tissue anchors 32a and 32b, respectively, are deployed in succession with no intervening anchor between anchors 32a and 32b, and a distance between anchors 32a and 32b is between 2.5 and 15 mm, e.g., between 2.5 and 9 mm, e.g., 8 mm.

Reference is now made to FIGS. 4C and 4E. It is to be noted that first and second tissue anchors 32a and 32b are deployed from within the lumen of channel 18 contained within the lumen of sleeve 26, while at least a proximal portion of sleeve 26 is surrounded by catheter 14, as shown.

Reference is again made to FIG. 4E. As shown, each of anchors 32a and 32b defines a respective central longitudinal axis 232a and 232b. Anchors 32a and 32b are substantially parallel (e.g., parallel) with respect to each other. For some applications, anchors 32a and 32b are implanted with respect to each other such that axes 232a and 232b are substantially parallel. For some applications, anchors 32a and 32b are implanted with respect to each other such that axes 232a and 232b are at angle of between 0 and 45 degrees, e.g., between 0 and 30 degrees, e.g., between 0 and 20 degrees.

For some applications, forming of portion 257 into the generally "U"-shaped portion (i.e., a portion having a concavity with respect to tissue of annulus 240 at planar surface 255) comprises anchoring anchor 32b into tissue of annulus 240 at planar surface 255. Anchors 32a and 32b are implanted in tissue of annulus 240 along a common plane (i.e., planar surface 255) and extend in substantially the same direction (i.e., anchors 32a and 32b extend substantially parallel with respect to each other). First and second anchors 32a and 32b extend in the substantially same direction despite that first tissue anchor 32a is deployed through end wall 251 transverse to side wall 253. That is, first and second anchors 32a and 32b extend in the substantially same direction while first tissue anchor 32a is deployed through end wall 251 transverse to side wall 253.

For some applications, a maximum distance L10 between first tissue anchor 32a and a point of anchoring of second tissue anchor 32b is provided by the length of sleeve 26 that has been decoupled from the portion of channel 18 (e.g., by the distance that channel 18 has been retracted from sleeve 26, e.g., between 3 and 15 mm, e.g., 8 mm). That is, for some applications, second tissue anchor 32b may be placed anywhere within a circle having a radius that equals L10, centered on the first tissue anchor.

For some applications, a stiffening element 1926 is provided during the implantation of sleeve 26, and for some applications, the stiffening element facilitates positioning of portions of the sleeve and/or anchors 32, such as positioning of subsequent portions and/or anchors following positioning of previous portions and/or anchors. For example, and as shown in FIG. 4D, by resisting compression, stiffening element 1926 biases the positioning of the distal end of channel 18 (and thereby the position at which the second tissue anchor will be deployed) toward the perimeter of the circle described hereinabove that is centered on the first tissue anchor. That is, by resisting compression, stiffening element 1926 biases the second tissue anchor toward being disposed a distance L10 from the first tissue anchor. Due to, or independently from, this compression-resisting feature of stiffening element 1926, stiffening element 1926 typically maintains an overall length of sleeve 26, the length of the sleeve having typically been selected in response to measurement of the annulus on which it is to be implanted.

By resisting bending, stiffening element 1926 may further bias the positioning of the distal end of channel 18 (and thereby the position at which the second tissue anchor will be deployed) toward a particular sector of the circle. For some applications, by resisting compression and bending, stiffening element 1926 biases the positioning of the distal end of channel 18 (and thereby the position at which the second tissue anchor will be deployed) toward a particular sector of the perimeter of the circle, i.e., toward an arc 1928.

For some applications, by resisting bending, stiffening element 1926 biases sleeve 26 (and portions thereof) toward being straight, and thereby biases positioning of the distal end of channel 18 (and thereby the position at which the next anchor will be deployed) toward being on a line defined by at least the two preceding anchors (e.g., the two preceding anchors define a line segment of the line therebetween). FIG. 4E includes a schematic view illustrating first tissue anchor 32a, second tissue anchor 32b, and a corresponding portion of sleeve 26 having been anchored to annulus 240. A line 1927 is defined by the anchors 32a and 32b, stiffening element 1926 (not shown in this view) biasing a subsequent portion of sleeve 26 (and thereby subsequent anchors) to be disposed along line 1927. A desired position of a subsequent anchor is shown by cross 1930. This desired position is at the annulus, rather than closer to the center of the valve (e.g., the leaflets of the valve). Anatomical constraints and/or application of force by the operating physician oppose this biasing, such that the subsequent anchor is anchored at cross 1930. For such applications, the presence of stiffening element 1926 thereby facilitates placement of the subsequent anchor at annulus 240, as opposed to placement closer to the center of valve 230. It is to be noted that stiffening element 1926 biases structure 222 (e.g., sleeve 26 thereof) to assume a shape that is different to that of the native valve and/or native annulus. That is, stiffening element 1926 biases structure 222 (e.g., sleeve 26 thereof) to not conform to the shape of the native valve and/or native annulus.

For some applications, stiffening element 1926 helps maintain the shape of portion 257. That is, stiffening element 1926 helps maintain the general "U"-shape of portion 257 (i.e., the portion having a concavity with respect to tissue of annulus 240 at planar surface 255). For some applications, stiffening element 1926 helps bias portion 257 into the shape. Alternatively, for some applications, the shape of portion 257 as shown in FIG. 4E, is achieved without stiffening element 1926. For example, a distal end of stiffening element 1926 is disposed proximally to portion 257. For other applications, structure 222 does not comprise stiffening element 1926. For some applications, sleeve 26 at at least portion 257 is resilient.

It is to be noted, however, that stiffening element 1926 is shown by way of illustration and not limitation, and that for some applications of the present invention structure 222 is provided without stiffening element 1926.

FIG. 4F shows the entire length of sleeve 26 having been anchored, via a plurality of anchors 32, to annulus 240, as described hereinabove. As shown, the plurality of remaining anchors 32 are implanted while maintaining distal portion 257 of sleeve 26 (i.e., the portion of the sleeve that is proximal to end wall 251) in a generally "U"-shaped portion (i.e., a portion having a concavity with respect to tissue of annulus 240 at planar surface 255).

The deployment manipulator (i.e., deployment manipulator 61 described herein but not shown in FIG. 4F) is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. Then, system 10 is removed, leaving behind guide member 86.

FIG. 4G shows an adjustment tool 87 being threaded over and advanced along guide member 86. Adjustment tool 87 typically comprises a rotation tool, and is configured to actuate (e.g., rotate) adjustment mechanism 40, so as to contract contracting member 226, and thereby sleeve 26, as described hereinabove. Typically, adjustment mechanism 40 comprises a housing which houses a spool, i.e., a rotatable structure, to which a first end of contracting member 226 is coupled. Typically, the spool is configured to adjust a perimeter of annuloplasty ring structure 222 by adjusting a degree of tension of contracting member 226 that is coupled at a first portion of member 226 to the spool. The contracting member 226 extends along sleeve 26 and a second portion of contracting member 226 (i.e., a free end portion) is coupled to a portion of sleeve 26 such that upon rotation of the spool in a first rotational direction, the portion of sleeve 26 is pulled toward adjustment mechanism 40 in order to contract annuloplasty ring structure 222. It is to be noted that the contraction of structure 222 is reversible. That is, rotating the spool in a second rotational direction that opposes the first rotational direction used to contract the annuloplasty structure, unwinds a portion of contracting member 226 from around the spool. Unwinding the portion of contracting member 226 from around the spool thus feeds the portion of contracting member 226 back into a lumen of sleeve 26 of structure 222, thereby slackening the remaining portion of contracting member 226 that is disposed within the lumen sleeve 26. Responsively, the annuloplasty structure gradually relaxes and expands (i.e., with respect to its contracted state prior to the unwinding).

The spool typically comprises a locking mechanism that prevents rotation of the spool after contracting member 226 has been tightened. For example, locking techniques may be used that are described with reference to FIG. 4 of U.S. Pat. No. 8,241,351 to Cabiri.

Tool 87 and is used to rotate the spool of adjustment mechanism 40 in order to tighten structure 222 by adjusting a degree of tension of contracting member 226 (not shown in FIG. 4G. Once the desired level of adjustment of structure 222 is achieved (e.g., by monitoring the extent of regurgitation of the valve under echocardiographic and/or fluoroscopic guidance), rotation tool 87 and guide member 86 are removed from the heart. For some applications, a distal portion of guide member 86 may be left within the heart of the patient and the proximal end may be accessible outside the body, e.g., using a port. For such applications, adjusting mechanism 40 may be accessed at a later stage following initial implantation and adjustment of ring structure 222.

As shown, sleeve 26 of ring structure 222 comprises a plurality of radiopaque markers 25, which are positioned along the sleeve at respective longitudinal sites to indicate anchor-designated target areas. The markers may provide an indication in a radiographic image (such as a fluoroscopy image) of how much of sleeve 26 has been deployed at any given point during an implantation procedure, in order to enable setting a desired distance between anchors 32 along the sleeve 26.

Alternatively, annuloplasty ring structure 222 is implanted by right or left thoracotomy, mutatis mutandis.

For some applications of the present invention, following implantation of sleeve 26 along the annulus, an excess portion of sleeve 26 may be present at the proximal portion of sleeve. In such applications, following removal of manipulator 61, a cutting tool (not shown) may be advanced within channel 18 and into the lumen of the excess portions of sleeve 26 (e.g., from within sleeve 26) in order to cut the sleeve proximal to the proximal-most-deployed anchor 32.

Reference is again made to FIGS. 4A-G. For anatomical reasons, a transluminal (e.g., transfemoral) approach to the mitral valve via transseptal puncture typically provides access more directly and/or easily to the region of the anterior commissure (e.g., including left fibrous trigone 242) than to the region of the posterior commissure (e.g., including right fibrous trigone 244). It may therefore be advantageous to position and anchor distal end wall 251 of sleeve 26 in the vicinity of the left fibrous trigone; the positioning of the first point of anchoring of structure 222 may be more difficult than the positioning of subsequent points of anchoring (e.g., due to guidance provided by sleeve 26 and/or stiffening element 1926; FIG. 4E). Due to this same reason of accessibility, it may also be advantageous to deliver adjustment tool 87 to the region of the anterior commissure (as shown in FIG. 4G).

System 10 (e.g., structure 222 thereof) is configured to facilitate exploitation of these two advantages: By adjustment mechanism 40 being disposed at a distal end of sleeve 26, and being movable away from the longitudinal axis of the sleeve, (1) the first tissue anchor may be driven through end wall 251 into the region of the anterior commissure, despite the adjustment mechanism having previously been obstructively positioned, and (2) the adjustment tool may be delivered to the region of the anterior commissure because the adjustment mechanism is disposed in that region.

Reference is made to FIG. 5, which is a schematic illustration of a state of a distal portion of system 10 within the heart of a subject, in accordance with some applications of the invention. As generally described hereinabove, (i) catheter 12 is steerable in a first plane, (ii) catheter 14 is steerable in a second plane that is typically perpendicular to the first plane, and (iii) distal portions of sleeve 26 are laid along the annulus of the native valve while proximal portions of the sleeve (and the distal end of manipulator 61, within the sleeve) are disposed at a nonzero angle with respect to the annulus. Thus, system 10 is configured to assume a multi-bend formation 2948 (e.g., handle portion 101 is configured to configure catheter 12, catheter 14, and structure 222 to assume the multi-bend formation) in which at least three domains 2950, and at least two bends 2952 separating the domains, are defined.

The formation includes (i) a first bend 2952a that separates a first domain 2950a of the formation from a second domain 2950b of the formation, and (ii) a second bend 2952b that separates the second domain from a third domain 2950c of the formation. Typically, the formation further includes a third bend 2952c that separates first domain 2950a from a fourth domain 2950d of the formation. First domain 2950a comprises at least (1) part of catheter 12 and (2) part of catheter 14 (i.e., at least a part of catheter 14 disposed within catheter 12), and typically further comprises at least part of sleeve 26 (i.e., at least part of sleeve 26 disposed within catheter 14). Second domain 2950b comprises at least part of catheter 14 (e.g., distal end portion 114 thereof), and at least part of sleeve 26 (e.g., the second domain comprises at least part of sleeve 26 disposed within a portion of catheter 14 that is exposed from catheter 12). Third domain 2950c comprises at least part of sleeve 26, and none of catheters 12 or 14 (i.e., the third domain comprises part of sleeve 26 that is disposed out of the distal end of catheter 14). In applications in which formation 2948 includes third bend 2952 and fourth domain 2950d, the fourth domain comprises at least (1) part of catheter 12 and (2) part of catheter 14 (i.e., at least a part of catheter 14 disposed within catheter 12), and may further comprise at least part of sleeve 26 (i.e., at least part of sleeve 26 disposed within catheter 14). Thus, domains 2950a and 2950d are typically of similar composition, but separated by third bend 2952c.

Thus, handle portion 101 may be considered to be configured:

to drive at least (i) part of catheter 12 and (ii) part of catheter 14 to define first domain 2950*a*, to drive at least part of catheter 14 that is disposed outside of catheter 12 to define second domain 2950*b*, to drive system 10 to define third domain 2950*c* from sleeve 26, and typically, to drive at least (i) part of catheter 12 and (ii) part of catheter 14 to define fourth domain 2950*d*.

Figure 6A:
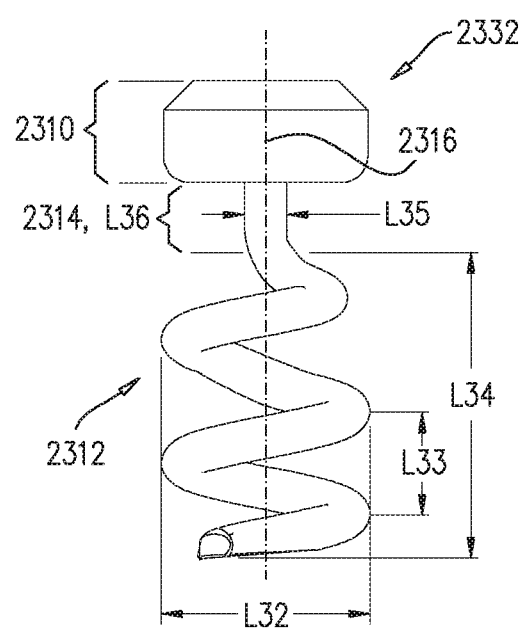
Figure 6B:
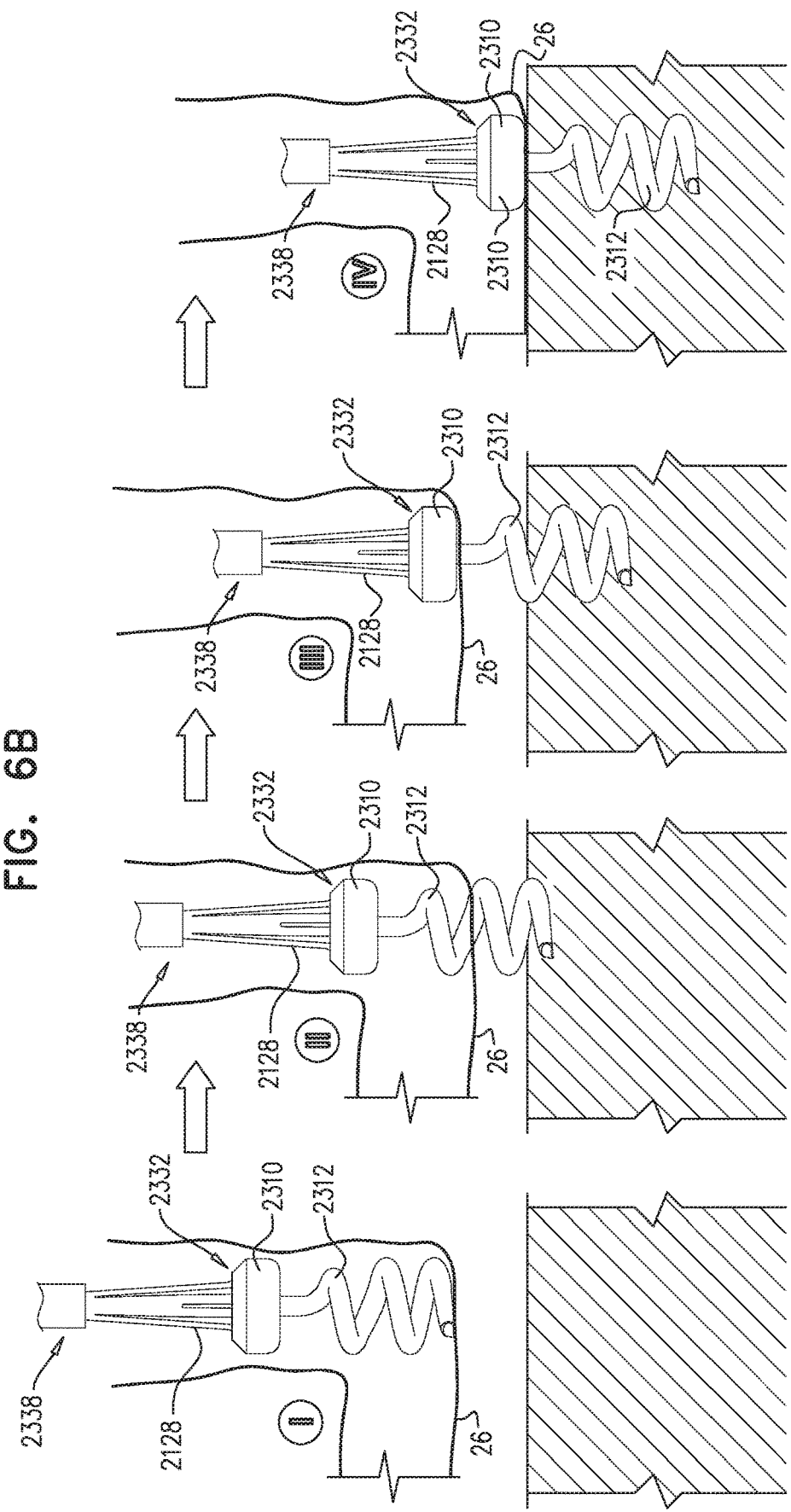

Reference is made to FIGS. 6A-C, which are schematic illustrations of a tissue anchor 2332 configured for anchoring sleeve 26 described hereinabove, in accordance with some applications of the present invention. Anchor 2332 has a coupling head 2310 configured to be coupled to a deployment element 2338, which has a locking mechanism 2128 disposed at a distal end thereof. Typically, deployment element 2338 (which comprises comprise deployment element 38, described herein) and a locking mechanism 2128. Locking mechanism 2128 is configured to selectively assume locked and unlocked states. When locking mechanism 2128 assumes the locked state, the locking mechanism prevents disengagement of rotating deployment element 2338 from the anchor which rotating deployment element 2338 currently engages. This locking allows deployment element 38 to proximally withdraw anchor 2332 if necessary, without coming disengaged therefrom. Disengagement is thus prevented even upon withdrawal of the rotating deployment element in the proximal direction. When the locking mechanism assumes the unlocked state, the locking mechanism does not prevent disengagement of the rotating deployment element from the anchor upon withdrawal of rotating deployment element 2338 in the proximal direction. The rotating deployment element thus can be disengaged and withdrawn from the anchor in a proximal direction. It is noted that even when the locking mechanism assumes the unlocked state, the rotating deployment element generally does not disengage from the anchor unless the rotating deployment element is withdrawn in the proximal direction.

For some applications, coupling head 2310 is alternatively or additionally configured to be coupled to, and/or used with, deployment manipulator 61, deployment element 38, and/or anchor driver 36 described hereinabove. Anchor 2332 provides a tissue coupling element 2312 (e.g., a helical tissue coupling element, as shown, or a screw). For some applications of the invention, anchor 32 described hereinabove, comprises anchor 2332 and/or anchors 32 and 2332 are interchangeable.

A proximal portion of coupling element 2312 comprises a vertical (and typically straight) proximal portion 2314 which is coupled to coupling head 2310 within 3 mm of a central longitudinal axis 2316 of tissue anchor 2332 (e.g., within 1 mm of axis 2316, such as on axis 2316). Proximal portion 2314 may alternatively comprise a proximal stem portion that couples coupling element 2312 to coupling head 2310. Vertical proximal portion 2314 typically has a length L36 of 0.2-0.7 mm, and is typically more than 1.3 times as great as (e.g., between 2 and 10 times as great as, such as between 2 and 4 times as great as) a thickness of the fabric of sleeve 26. During anchoring of sleeve 26 by anchor 2332 (e.g., as shown in FIG. 6B), such a configuration of the positioning of portion 2314 at the center of coupling head 2310 facilitates rotation of tissue anchor 2332 with respect to sleeve 26 in a manner that prevents twisting of sleeve 26 during rotation. That is, once coupling element 2312 has passed far enough through sleeve 26 such that portion 2314 traverses the wall of the sleeve (as shown in stage (iii) of FIG. 6B), portion 2314 rotates freely within the wall of the sleeve. (For some applications in which portion 2314 is coupled to coupling head 2310 within 3 mm of, but not on, axis 2316, flexibility of the fabric of sleeve 26 facilitates such free rotation, by distorting as portion 2314 "wiggles".) Such a configuration allows anchor 2332 to be driven into the cardiac tissue, such that coupling head 2310 draws sleeve 26 closer to the cardiac tissue, without distorting (e.g., twisting, kinking, buckling, etc.) the sleeve (as shown by the transition from stage (iii) to stage (iv) of FIG. 6B). For some such applications, anchor 2332, coupling element 2312, and/or portion 2314 act as an integral washer and/or a screw with an integral washer, as is known in the hardware art.

Coupling head 2310 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Anchor driver 36 has a deployment element 38 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided by coupling head 2310 of anchor 2332 of FIGS. 6A-C.

Thus, anchor 2332, by way of illustration and not limitation, comprises a helical portion (i.e., tissue coupling element 2312) and a non-helically shaped portion (i.e., coupling head 2310 and vertical (and typically straight) proximal portion 2314).

Anchor 2332 has an anchor helix diameter L32 of between 0.2 and 0.3 cm, e.g., 0.25 cm. That is, the radius of the anchor helix from longitudinal axis 2316 is typically between 0.1 and 0.15 cm, e.g., 0.125 cm. Anchor 2332 has an anchor helix pitch L33 of between 0.1 and 0.2 cm, e.g., 0.12 cm. Anchor 2332 has an anchor helix length L34 of between 0.3 and 0.6 cm, such as 0.3 and 0.45 cm, e.g., 0.35 cm. Anchor 2332 has a helix wire thickness L35 of between 0.02 and 0.1 cm, e.g., 0.05 cm.

For some applications of the invention, torque-limiting apparatus 2300, coupled to anchor driver 36, prevents over-rotation of the anchor, penetration of tissue coupling element 2312 too deep into tissue, and/or damage to the tissue.

For some applications, a ratio between diameter L32 of the helix of anchor 2332 (cm) to torque (Ncm) is typically, but not necessarily 0.25/0.8, or 0.3125. For some applications, a ratio between pitch L33 of anchor 2332 (cm) to torque (Ncm) is typically, but not necessarily 0.12/0.8, or 0.15. For some applications, a ratio between length L34 of the helix of anchor 2332 (cm) to torque (Ncm) is typically, but not necessarily 0.35/0.8, or 0.4375. For some applications, a ratio between thickness L35 of the wire forming anchor 2332 (cm) to torque (Ncm) is typically, but not necessarily 0.05/0.8, or 0.0625.

Typically, but not necessarily, anchor 2332 comprises a biocompatible material such as stainless steel 316 LVM. For some applications, anchor 2332 comprises nitinol. For some applications, anchor 2332 is coated with a non-conductive material.

Figure 7:
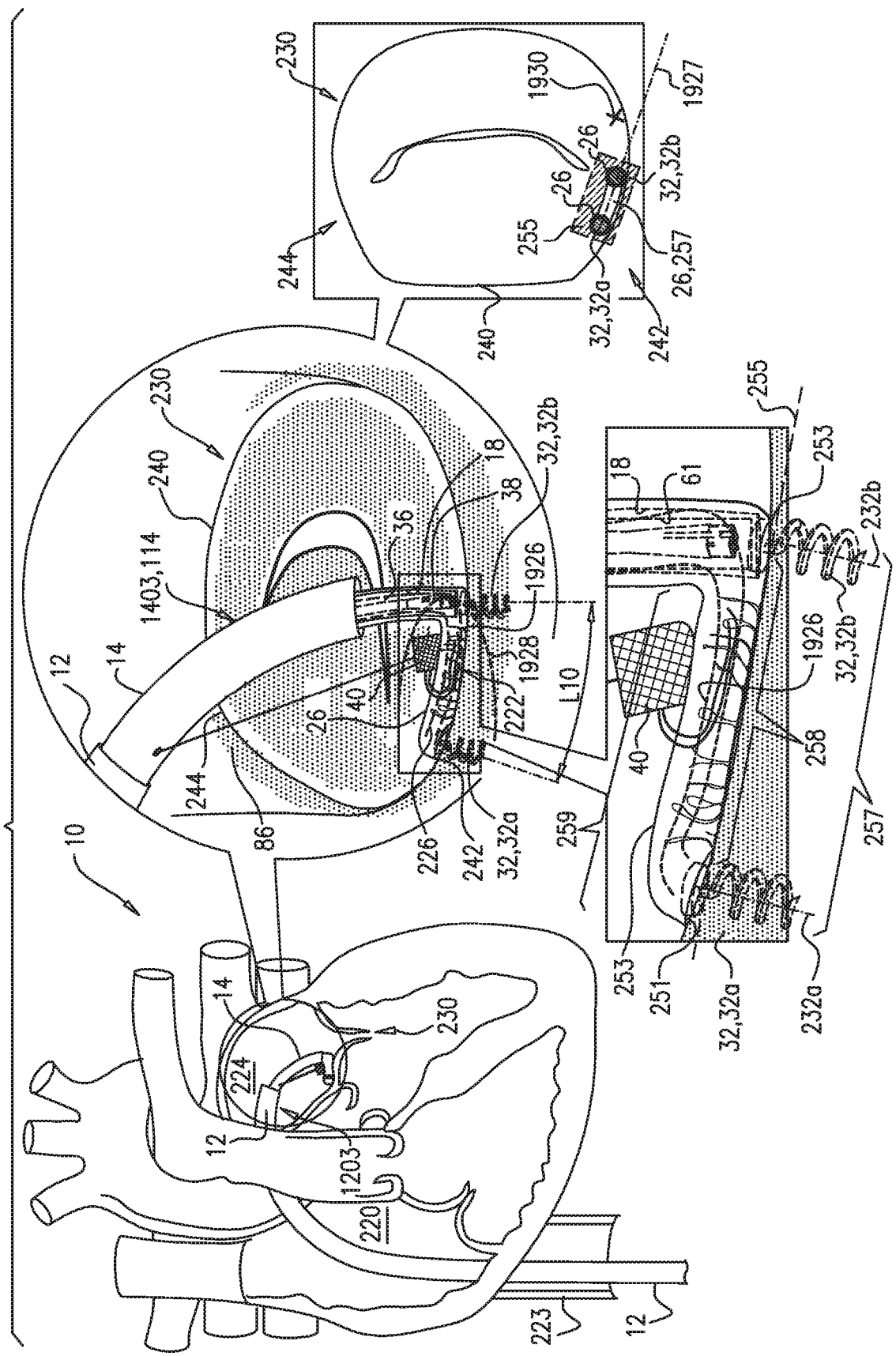
FIG. 7 is a schematic illustration of a step in the implantation of an annuloplasty ring structure to repair a mitral valve, in accordance with some applications of the invention.

Reference is now made to FIG. 7, which is a schematic illustration of a step in the implantation of an annuloplasty ring structure to repair a mitral valve, in accordance with some applications of the invention. It is to be noted that the steps for implanting structure 222 are similar to those described in FIGS. 4A-G and 5 with the exception of portion 257 being implanted along the surface of the tissue of annulus 240, while minimizing or eliminating the gap (defined as having a distance D1) shown in FIGS. 5D-G and 5. As shown in FIG. 7, for some applications, due to the elasticity of the fabric, portion 257 of sleeve 26 is generally flush with respect to planar surface 255 of annulus 240 despite that first tissue anchor 32a is deployed through end wall 251 transverse to side wall 253 in substantially the same direction (as described hereinabove with reference to FIG. 4E). In such a manner a gap is minimized or eliminated between portion 257 and the tissue of annulus 240 at planar surface 255. That is, for some applications, part 258 of portion 257 is positioned adjacent, alongside, and touching the tissue of annulus 240.

Thus, in such an application of the present invention, structure forms a shape in which: (1) first part 258 of the lateral surface of portion 257 of side wall 253, is crimped or ruffled, while (2) second part 259 of the lateral surface of portion 257 of side wall 253 (i.e., opposite first part 258) is more tensioned and less curved than first part 258.

That is, first part 258 has (1) a higher degree of curvature than second part 259, and (2) a smaller radius of curvature than second part 259. Additionally, second part 259 has (1) a smaller degree of curvature than first part 258, (2) a greater degree of tension than first part 258, and (3) a larger radius of curvature than first part 259.

It is to be noted that stiffening element 1926 is shown extending through portion 257 by way of illustration and not limitation. For example, for some applications, the shape of portion 257 as shown in FIG. 7, is achieved without stiffening element 1926. For example, a distal end of stiffening element 1926 is disposed proximally to portion 257. For other applications, structure 222 does not comprise stiffening element 1926. That is, without stiffening element 1926 in portion 257, portion 257 has a greater flexibility to achieve the ruffled and crimped configuration of part 258. For some applications, such flexibility is due to sleeve 26 comprising a fabric.

Reference is now made to FIGS. 4D-E and 7. As described hereinabove, the shape of portion 257 is achieved in situ actively by flexing sleeve 26 prior to deploying the second anchor 32b. For other applications, the shape of portion 257 is achieved passively in response to releasing portion 257 from channel 18 followed by anchoring wall 253 with second anchor 32b.

Reference is made to FIGS. 1-7. It is to be noted that following implantation of the annuloplasty structures described herein, the dimensions of the annuloplasty structures may be adjusted remotely and while the patient is not on a cardio-pulmonary bypass pump (i.e., with a beating heart), under fluoroscopy and/or echo guidance.

Although annuloplasty structure 222 has been described hereinabove as comprising a partial annuloplasty ring, in some embodiments of the present invention, the ring instead comprises a full annuloplasty ring.

It is to be further noted that system 10 and catheters 12 and 14 may be advanced using a (1) trans-septal procedure in which the system is advanced through vasculature of the patient at any suitable access location (e.g., femoral vein), (2) a minimally-invasive transapical approach, (3) a minimally-invasive transatrial approach (e.g., an intercostal approach), or (4) a surgical, open-heart approach. Furthermore, for some applications, the systems described herein are not steerable and may comprise straight elements (e.g., in a surgical, open-heart procedure).

It is to be further noted that system 10 and catheters 12 and 14 for repairing a dilated annulus of the patient may be used to treat any cardiac valve of the patient, e.g., the aortic valve, the pulmonary valve, the mitral valve, and the tricuspid valve. It is to be still further noted that systems described herein for treatment of valves may be used to treat other annular muscles within the body of the patient. For example, the systems described herein may be used in order to treat a sphincter muscle within a stomach of the patient.

It is further noted that the scope of the present invention includes the use of system 10 and catheters 12 and 14 (or subcomponents thereof) and methods described hereinabove on any suitable tissue of the patient (e.g., stomach tissue, urinary tract, and prostate tissue).

In some embodiments of the present invention, system 10 is used to treat an atrioventricular valve other than the mitral valve, i.e., the tricuspid valve. In these embodiments, annuloplasty structure 222 and other components of system 10 described hereinabove as being placed in the left atrium are instead placed in the right atrium. Although annuloplasty structure 222 is described hereinabove as being placed in an atrium, for some application the ring is instead placed in either the left or right ventricle.

Additionally, the scope of the present invention includes embodiments described in the following applications, which are incorporated herein by reference. In an embodiment, techniques and apparatus described in one or more of the following applications are combined with techniques and apparatus described herein:

U.S. patent application Ser. No. 12/341,960 to Cabiri, entitled, "Adjustable partial annuloplasty ring and mechanism therefor," filed on Dec. 22, 2008, which published as US Patent Application Publication 2010/0161047 and issued as U.S. Pat. No. 8,241,351;

U.S. patent application Ser. No. 12/435,291 to Maisano et al., entitled, "Adjustable repair chords and spool mechanism therefor," filed on May 4, 2009, which published as US Patent Application Publication 2010/0161041 and issued as U.S. Pat. No. 8,147,542;

U.S. patent application Ser. No. 12/437,103 to Zipory et al., entitled, "Annuloplasty ring with intra-ring anchoring," filed on May 7, 2009, which published as US Patent Application Publication 2010/0286767, and which issued as U.S. Pat. No. 8,715,342;

U.S. patent application Ser. No. 12/548,991 to Maisano et al., entitled, "Implantation of repair chords in the heart," filed on Aug. 27, 2009, which published as US Patent Application Publication 2010/0161042, and which issued as U.S. Pat. No. 8,808,368;

PCT Patent Application PCT/IL2009/001209 to Cabin et al., entitled, "Adjustable annuloplasty devices and mechanisms therefor," filed on Dec. 22, 2009, which published as PCT Publication WO 10/073246;

PCT Patent Application PCT/IL2010/000357 to Maisano et al., entitled, "Implantation of repair chords in the heart," filed on May 4, 2010, which published as WO 10/128502;

PCT Patent Application PCT/IL2010/000358 to Zipory et al., entitled, "Deployment techniques for annuloplasty ring and over-wire rotation tool," filed on May 4, 2010, which published as WO 10/128503; and/or PCT Patent Application PCT/IL2012/050451 to Sheps et al., entitled, "Controlled steering functionality for implant-delivery tool," filed on Nov. 8, 2012, and which published as WO 13/069019.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for repairing a cardiac valve, the apparatus comprising:
   a flexible annuloplasty structure having a sleeve with an elongated tubular side wall and at least one distal tip;
   a first tissue anchor passing through the distal tip of the sleeve; and
   a second tissue anchor passing through a section of the tubular side wall, the first and second tissue anchors are arranged such that:
      (a) the first and second tissue anchors are disposed with no intervening anchors therebetween;
      (b) the first and second tissue anchors extend in a substantially same direction; and
      (c) a longitudinal portion of the tubular side wall is disposed between the first tissue anchor and the second tissue anchor, and has a first lateral part and a second lateral part opposite the first lateral part, the first lateral part being closer to the first and second tissue anchors than the second lateral part is to the first and second tissue anchors,
   wherein the second lateral part of the longitudinal portion has a degree of tension that is larger than a degree of tension of the first lateral part of the longitudinal portion.

2. The apparatus according to claim 1, wherein the second tissue anchor is disposed between 0 and 20 degrees with respect to the first tissue anchor.

3. The apparatus according to claim 1, wherein the second tissue anchor is disposed between 2.5 and 9 mm from the first tissue anchor.

4. The apparatus according to claim 1, wherein the second tissue anchor is disposed between 0 and 45 degrees with respect to the first tissue anchor.

5. The apparatus according to claim 1, further comprising an adjustment mechanism configured to adjust a perimeter of the flexible annuloplasty structure.

6. The apparatus according to claim 1, further comprising a contracting member extending along a length of the sleeve, the contracting member being configured to adjust a perimeter of the flexible annuloplasty structure.

7. The apparatus according to claim 1, wherein the first and second tissue anchors are disposed consecutively and extend in a substantially same direction.

8. The apparatus according to claim 7, wherein the first and second tissue anchors are disposed in parallel.

9. A system for repairing a cardiac valve, the system comprising:
   a flexible annuloplasty structure having a sleeve with an elongated tubular side wall and at least one distal tip;
   a first tissue anchor passable through the distal tip of the sleeve; and
   a second tissue anchor passable through the tubular side wall;
   wherein the system is configured to be implantable at the cardiac valve such that a portion of the tubular side wall that is between the first and second tissue anchors assumes a shape in which:
      the portion has a first part of a lateral surface of the tubular side wall and a second part of the lateral surface of the tubular side wall opposite the first part, wherein the second part of the lateral surface of the tubular side wall has a degree of tension that is larger than a degree of tension of the first part of the lateral surface of the tubular side wall.

10. The system according to claim 9, wherein the second tissue anchor is positionable between 2.5 and 9 mm from the first tissue anchor.

11. The system according to claim 9, wherein the second tissue anchor is positionable between 0 and 45 degrees with respect to the first tissue anchor.

12. The system according to claim 9, wherein the second tissue anchor is positionable between 0 and 20 degrees with respect to the first tissue anchor.

13. The system according to claim 9, further comprising an adjustment mechanism configured to adjust a perimeter of the flexible annuloplasty structure.

14. The system according to claim 9, further comprising a contracting member extending along a length of the sleeve, the contracting member being configured to adjust a perimeter of the flexible annuloplasty structure.

15. The system according to claim 9, wherein the first and second tissue anchors are configured to be deployed consecutively and extend in a substantially same direction.

16. The system according to claim 15, wherein the first and second tissue anchors are deployable in parallel.

17. An system for repairing a cardiac valve, the system comprising:
   a flexible structure having an elongated tubular side wall;
   a first tissue anchor configured to pass through a first portion of the flexible structure; and
   a second tissue anchor configured to pass through a second portion of the flexible structure;
   wherein the system is configured such that, when implanted at the cardiac valve, the tubular side wall between the first and second tissue anchors has a first part of a lateral surface of the tubular side wall with a degree of tension that is less than a larger degree of tension of a second part of the lateral surface of the tubular side wall opposite the first part.

18. The system according to claim 17, further comprising an adjustment mechanism configured to adjust a perimeter of the flexible annuloplasty structure.

19. The system according to claim 17, further comprising a contracting member extending along a length of the sleeve, the contracting member being configured to adjust a perimeter of the flexible annuloplasty structure.

20. The system according to claim 17, wherein the first and second tissue anchors are configured to be deployed consecutively and extend in a substantially same direction.

* * * * *